(12) United States Patent
Shearman et al.

(10) Patent No.: US 9,451,802 B2
(45) Date of Patent: Sep. 27, 2016

(54) HELMET SYSTEM AND METHODS

(71) Applicant: Fusar Technologies, Inc., Jersey City, NJ (US)

(72) Inventors: Ryan T Shearman, Jersey City, NJ (US); Daniel R Bersak, Queens, NY (US)

(73) Assignee: Fusar Technologies, Inc., Jersey City, NJ (US)

( * ) Notice: Subject to any disclaimer, the term of this patent is extended or adjusted under 35 U.S.C. 154(b) by 0 days.

(21) Appl. No.: 14/821,455

(22) Filed: Aug. 7, 2015

(65) Prior Publication Data

US 2016/0044276 A1 Feb. 11, 2016

Related U.S. Application Data

(60) Provisional application No. 62/034,896, filed on Aug. 8, 2014.

(51) Int. Cl.
| | |
|---|---|
| *H04N 5/225* | (2006.01) |
| *A42B 3/04* | (2006.01) |
| *A42B 3/06* | (2006.01) |
| *A42B 3/22* | (2006.01) |
| *A42B 3/30* | (2006.01) |
| *A61B 5/0476* | (2006.01) |
| *G08B 25/01* | (2006.01) |

(Continued)

(52) U.S. Cl.
CPC ............... *A42B 3/042* (2013.01); *A42B 3/046* (2013.01); *A42B 3/0426* (2013.01); *A42B 3/0433* (2013.01); *A42B 3/06* (2013.01); *A42B 3/22* (2013.01); *A42B 3/30* (2013.01); *A61B 5/0002* (2013.01); *A61B 5/01* (2013.01); *A61B 5/024* (2013.01); *A61B 5/0476* (2013.01); *A61B 5/0478* (2013.01); *A61B 5/11* (2013.01); *A61B 5/14553* (2013.01); *A61B 5/6803* (2013.01); *G08B 25/016* (2013.01); *H04N 5/2253* (2013.01); *H04N 5/772* (2013.01); *H04N 5/91* (2013.01)

(58) Field of Classification Search
None
See application file for complete search history.

(56) References Cited

U.S. PATENT DOCUMENTS

| | | | |
|---|---|---|---|
| 4,897,715 A | 1/1990 | Beamon, III | |
| 4,902,116 A | 2/1990 | Ellis | |

(Continued)

FOREIGN PATENT DOCUMENTS

| | | |
|---|---|---|
| CN | 200910145090 A1 | 3/2010 |
| CN | 201410776439 A1 | 12/2015 |
| KR | 2012/009880 A1 | 5/2014 |

*Primary Examiner* — Twyler Haskins
*Assistant Examiner* — Dwight C Tejano
(74) *Attorney, Agent, or Firm* — Run8 Patent Group; Peter Miller

(57) ABSTRACT

One variation of a method for recording accidents includes: in a first mode, capturing a second video frame at a second time, storing the second video frame with a first sequence of video frames, captured over a buffer duration, in local memory in the helmet, removing a first video frame captured outside of the buffer duration from local memory, and rendering a subregion of the second video frame on a display arranged within the helmet; in response to detection of an accident involving the helmet, transitioning from the first mode into a second mode; in the second mode, capturing a second sequence of video frames, and storing the second sequence of video frames exceeding the buffer duration in local memory; and generating a video file from the first sequence of video frames and the second sequence of video frames stored in local memory.

21 Claims, 7 Drawing Sheets

(51) Int. Cl.
*H04N 5/77* (2006.01)
*H04N 5/91* (2006.01)
*A61B 5/00* (2006.01)
*A61B 5/01* (2006.01)
*A61B 5/024* (2006.01)
*A61B 5/0478* (2006.01)
*A61B 5/11* (2006.01)
*A61B 5/1455* (2006.01)

(56) References Cited

U.S. PATENT DOCUMENTS

| | | | |
|---|---|---|---|
| 5,006,072 A | 4/1991 | Letovsky | |
| 5,091,719 A | 2/1992 | Beamon, III | |
| 5,420,828 A | 5/1995 | Geiger | |
| 5,453,877 A | 9/1995 | Gerbe | |
| 5,537,092 A | 7/1996 | Suzuki | |
| 5,646,784 A | 7/1997 | Wilson | |
| 5,835,247 A | 11/1998 | Monnier | |
| 6,798,392 B2 * | 9/2004 | Hartwell | A42B 3/046 345/158 |
| 6,859,327 B2 | 2/2005 | Del Bianco | |
| 6,978,162 B2 | 12/2005 | Russell | |
| 8,692,886 B2 | 4/2014 | Ennis | |
| 8,810,482 B2 | 8/2014 | Abdollahi | |
| 9,001,005 B2 | 4/2015 | Abdollahi | |
| 9,060,221 B1 | 6/2015 | Kaplan | |
| 9,247,779 B1 * | 2/2016 | Aloumanis | G08G 1/137 |
| 2008/0088527 A1 | 4/2008 | Fujimori | |
| 2008/0239080 A1 * | 10/2008 | Moscato | A42B 3/0426 348/148 |
| 2009/0016418 A1 | 1/2009 | Silver | |
| 2009/0040296 A1 | 2/2009 | Moscato | |
| 2009/0109286 A1 | 4/2009 | Ennis | |
| 2011/0037638 A1 | 2/2011 | Chen | |
| 2013/0093585 A1 | 4/2013 | Ambani | |
| 2013/0215281 A1 | 8/2013 | Hobby | |
| 2013/0305437 A1 * | 11/2013 | Weller | A42B 3/0406 2/422 |
| 2014/0167986 A1 | 6/2014 | Parada | |
| 2014/0273863 A1 | 9/2014 | Luizzi | |
| 2014/0362244 A1 | 12/2014 | Martin | |
| 2016/0107572 A1 * | 4/2016 | Weller | B60R 1/00 348/36 |

* cited by examiner

HELMET SYSTEM AND METHODS

CROSS-REFERENCE TO RELATED APPLICATIONS

This Application claims the benefit of U.S. Provisional Application No. 62/034,896, filed on 8, Aug. 2014, which is incorporated in its entirety by this reference.

TECHNICAL FIELD

This invention relates generally to the field of helmets, and more specifically to a new and useful helmet system and methods in the field of helmets.

DESCRIPTION OF THE EMBODIMENTS

The following description of the embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Helmet System

Figure 1:
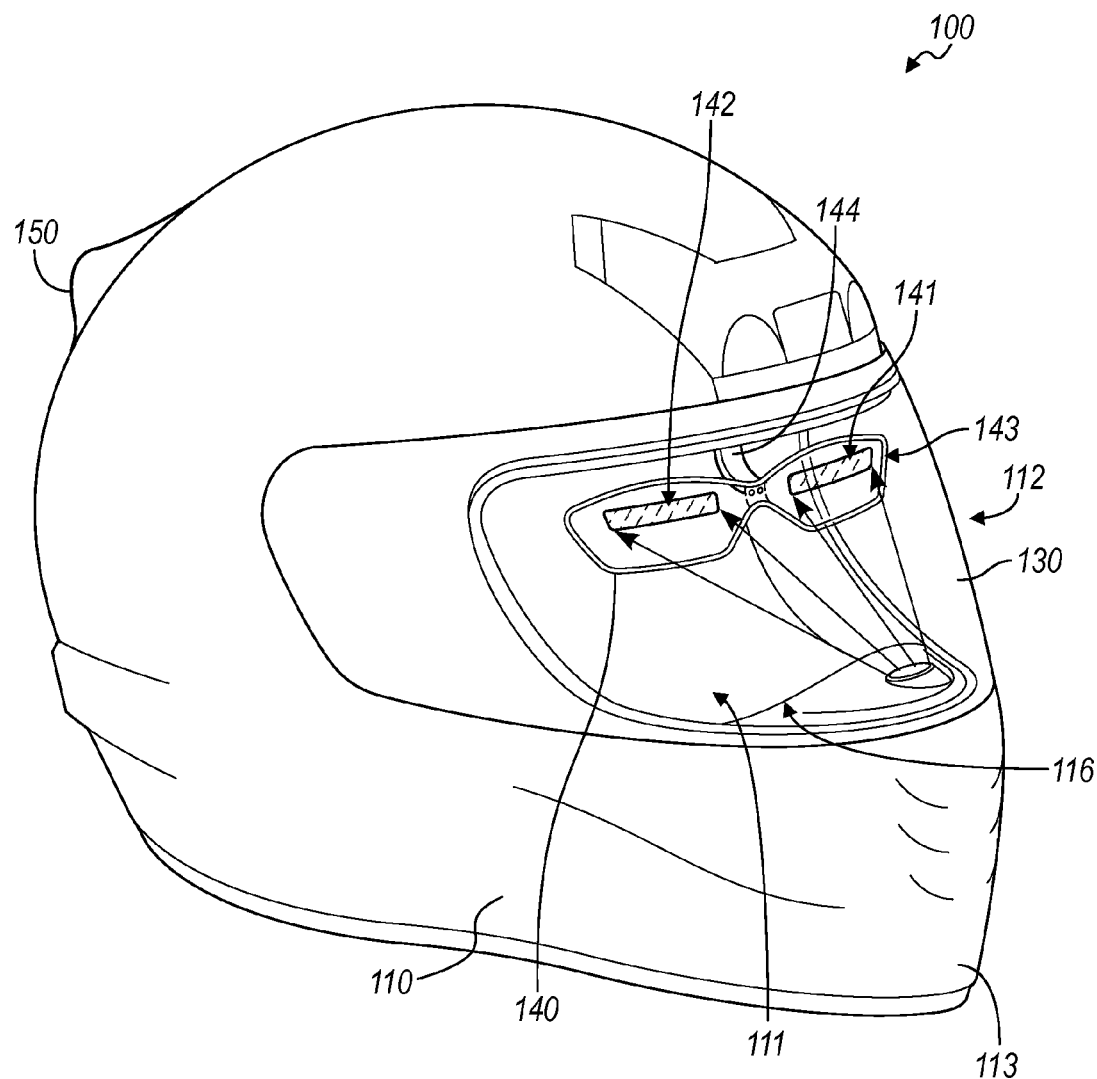
FIG. 1 is a schematic representation of a helmet system.

As shown in FIG. 1, a helmet system 100 includes: a shell 110 defining an interior volume and an aperture 112 proximal an anterior end of the shell 110; a primary visor 130 coupled to the shell 110 and transiently arranged over the aperture 112; a secondary visor 140 arranged between the aperture 112 and the interior volume in, including an elongated translucent member 143 suspended from the shell 110, and defining a first discrete reflective region 141 on a right side of the elongated translucent member 143 and a second discrete reflective region 142 on a left side of the elongated translucent member 143; a camera coupled to the shell 110 and defining a field of view extending outwardly from a posterior end of the shell 110; and a projection system 160 projecting an image onto the first discrete reflective region 141 and onto the second discrete reflective region 142, the image including a subregion of a video frame recorded by the camera, the secondary visor 140 reflecting the image toward the interior volume 111.

Figure 3:
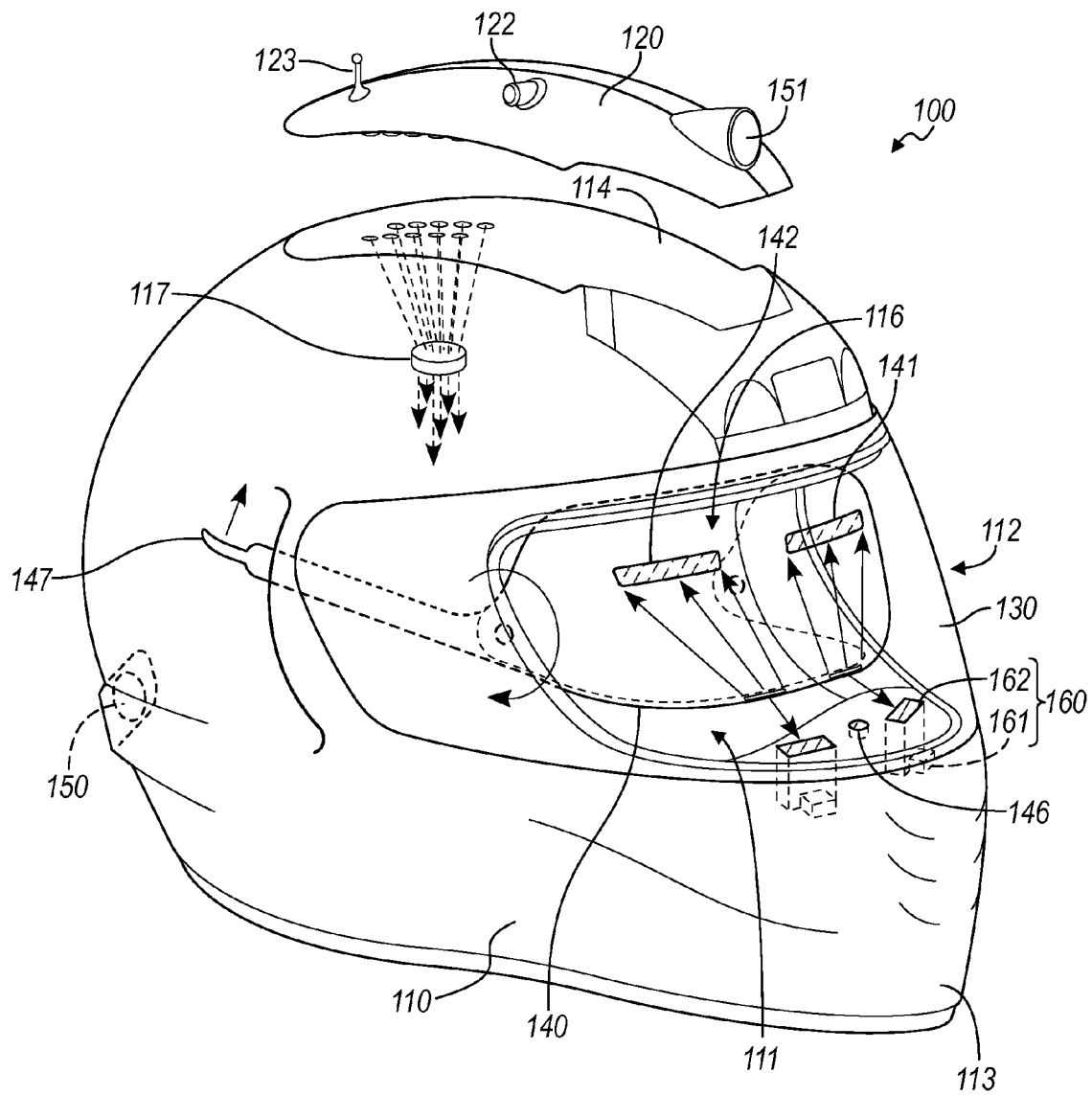
FIG. 3 is a schematic representation of one variation of the helmet system.

As shown in FIG. 3, one variation of the helmet system 100 includes: a shell defining an interior volume in and an aperture proximal an anterior end of the shell 110; a primary visor 130 coupled to the shell 110 and transiently arranged over the aperture 112; a secondary visor 140 including an optical element, operable between a retracted position and an active position, arranged between a dorsal region of the shell no and the interior volume 111 in the retracted position, and arranged between the aperture 112 and the interior volume 111 in the active position; a camera arranged on the shell 110 and defining a field of view opposite the aperture 112; and a projection system 160 transitioning from a standby mode to an active mode in response to transition of the secondary visor 140 from the retracted position to the active position and projecting an image toward the optical element in the active mode, the image including a subregion of a video frame recorded by the camera, the optical element reflecting the image toward the interior volume 111.

1.1 Applications

Generally, the helmet system 100 functions to capture images of a field behind the helmet system 100 and to display a form of these images onto a secondary visor 140 substantially in real-time, thereby enabling a user immediate visual access to the field behind him while looking forward. The helmet system 100 includes: a rear-facing camera 150 that captures images of the rear field behind the helmet system 100; a primary visor 130 that functions to shield a user's face from air, moisture, or debris during use; a secondary visor 140 arranged between the primary visor 130 and the user and displaying forms (e.g., cropped forms) of rear field images captured by the rear-facing camera 150; and a shell supporting these components. The primary visor 130 covers all or a portion of an aperture at the front of the shell 110 and can be raised and lowered independently of the secondary visor 140 during use, such as for improved air flow through the helmet. The secondary visor 140 can be statically mounted within the helmet and can display or project rear field images, telemetry and systems data, and/or navigation data, etc. for visual consumption by a user despite the position of the primary visor 130. Alternatively, the secondary visor 140 can be adjustable within the helmet, such as pivotable between a retracted position and an active position, to disable and enable display of these data, respectively, despite the position of the primary visor 130.

In one variation, the secondary visor 140 includes a translucent member that is statically mounted to the shell 110 ahead of the user's eyes with limited adjustability range and defining a perimeter within a user's field of view when looking out from the helmet system 100. For example, in this variation, the secondary visor can include a substantially planar translucent member. In another variation, the secondary visor 140 includes a translucent member that extends outside of the user's field of view when looking (straight) out from the helmet and wraps around the user's eyes (e.g., in the active position). In these variations, the secondary visor 140 defines one or more active areas that display or reflect images—output by the projection system 160—within the user's field of view when looking out from the helmet system 100 such that content thus displayed is visually accessible by the user without requiring the user to move his eyes or requiring the user to move his eyes only a relatively minimal angular distance (e.g., less than 10° upward). Specifically, the projection system 160 and the secondary visor 140 can cooperate to render an image proximal the center of the user's visual field. The projection system 160 can also generate cropped images output from video frames captured by the rear-facing camera 150, generate images from telemetry data received from an external wirelessly-connected device (e.g., a motorcycle, a smartphone), and/or generate composite images from rear field images and telemetry, navigation, or other (textual) data, etc. and then project these images on the secondary visor 140—such as proximal the center of the user's visual field—substantially in real-time.

The helmet system 100 can define a motorcycle helmet, an all-terrain-vehicle helmet, an automobile racing helmet, a skiing helmet, a snowboarding helmet, a snowmobile helmet, a bicycle helmet, a firefighting helmet, a disaster-relief helmet, or any other suitable form factor for any other suitable environment or application. However, for brevity, the helmet system 100 is described herein in the context of a motorcycle helmet. Furthermore, an individual wearing the helmet system 100 is referred to herein as "the user."

1.2 Shell

The shell 110 of the helmet system 100 defines an interior volume in and an aperture proximal an anterior end of the shell 110. Generally, the shell 110 functions to support the primary visor 130, the secondary visor 140, the projection system 160, and other components of the helmet system 100 and to provide head and/or face protection for the user in the event of an impact.

The shell 110 can define a full-face helmet including an interior volume in termination at a head opening to receive a user's head and a viewing aperture through which the user may look outwardly from the helmet during use, wherein the head opening and the viewing aperture are separated by a chin bar 113. In this implementation, the primary visor 130 can be pivotably mounted to the shell 110 and can selectively close (e.g., cover, seal) the viewing aperture. Alternatively, the shell 110 can define a three-quarter helmet, wherein the head opening and the viewing aperture are physically coextensive (i.e., define a single aperture) and the shell 110 covers the back of the user's head and ears when worn but excludes a chin bar 113. Yet alternatively, the shell 110 can define a half helmet. However, the shell 110 can define a helmet of any other suitable type or geometry.

In one implementation, the shell 110 includes a rigid outer shell, a rigid inner shell, and a compressible (e.g., foam) core between the inner and outer rigid shells. The shell 110 can be of composite (e.g., carbon fiber, para-aramid synthetic fiber), a polymer (e.g., nylon), a metal (e.g., aluminum), and/or any other suitable material. However, the shell 110 can define any other suitable structure and can be of any other suitable material(s). The shell 110 can also include an overhead lining 116 (or "comfort lining") inside the interior volume in of the shell 110. However, the shell 110 can be of any other material and define any other suitable structure.

1.3 Fairing

The shell 110, the primary visor 130, the secondary visor 140, the projection system 160, and other components of the helmet system 100 can be integrated into a single unit. Alternatively, components of the helmet system 100 can be selectively installed and removed from the shell 110.

In one variation, the shell 110 defines a fairing receptacle 114 on its exterior dorsal side, and the helmet system 100 further includes a fairing 120 transiently coupled to the fairing receptacle 114, as shown in FIG. 3. In this variation, the fairing 120 can mount to the outside of the shell 110, such as centered on top of the shell no behind the primary visor 130, and can house various components of the helmet system 100. For example, the fairing 120 can house any one or more of: a processor 124 executing the method described below; a display driver 163 of the projection system 160; the camera 150 (e.g., directed outwardly from a posterior end of the fairing 120) and a wide-angle lens; a forward-facing camera 151, infrared emitter, infrared filter, and/or infrared detector; inertial sensors 125 (e.g., an accelerometer, gyroscope, tilt sensor, and/or compass); environmental sensors (e.g., a humidity sensor, an ambient light level sensor); biometric sensors (e.g., a skin temperature sensor, a heart rate sensor, a pulse oximetry sensor, a set of dry electroencephalogy sensors); a wireless communication module 123 that pairs with a local external device (e.g., a smartphone, a vehicle ridden by the user); a (rechargeable) battery 127, recharging circuitry, and/or an energy harvester (e.g., a solar panel, a turbine and dynamo); a local memory module 126 (e.g., a solid state hard drive or removable secure digital memory card); and/or a feedback module (e.g., a vibrator).

In this variation, the fairing 120 can be transiently mounted on (i.e., removable from) the shell 110 and can transiently connect to and communicate with one or more projectors of the projection system 160. In one example, the shell 110 includes one or more doors or flaps that open to reveal a fairing receptacle 114 configured to receive the fairing 120. In this example, the shell 110 can also include a wiring harness 117 extending from a connector in the fairing receptacle 114 to the interior volume 111, such as to one or more speakers 118 (or speaker receptacles), to a microphone 119, and/or to the projector(s), as shown in FIG. 3. The fairing 120 can engage the connector when installed and locked into the fairing receptacle 114. The display driver 163 arranged in the fairing 120 can thus transmit images to the projector via the wiring harness 117; the wireless communication module 123 can transmit and receive audio signals to the speaker(s) 118 and to the microphone 119, respectively, via the wiring harness 117; and the memory module 126 can receive biometric data from the skin temperature sensor, heart rate sensor, and/or dry electroencephalogy sensors via the wiring harness 117; etc.

Figure 4:
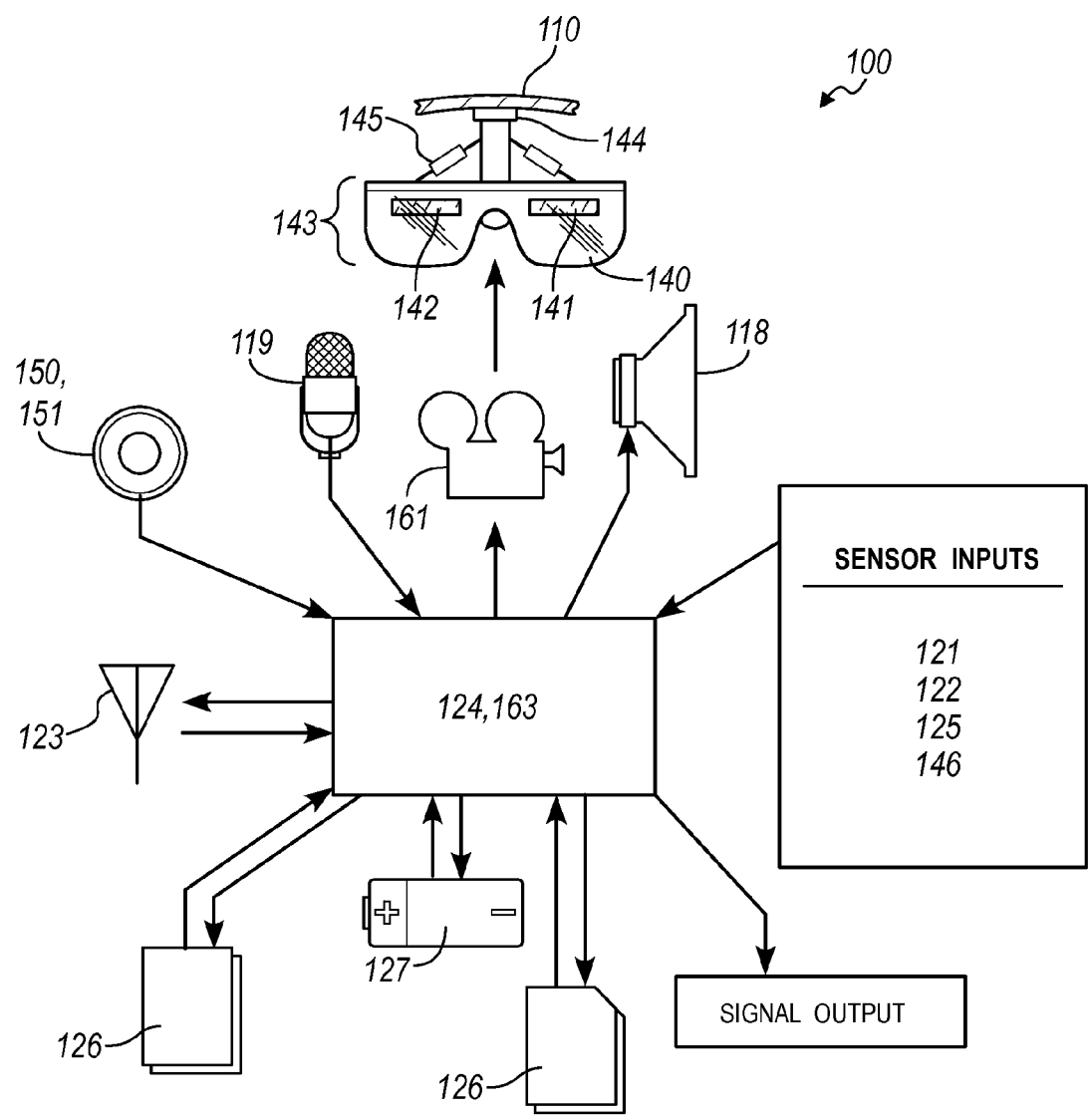
FIG. 4 is a schematic representation of one variation of the helmet system.
Figure 5:
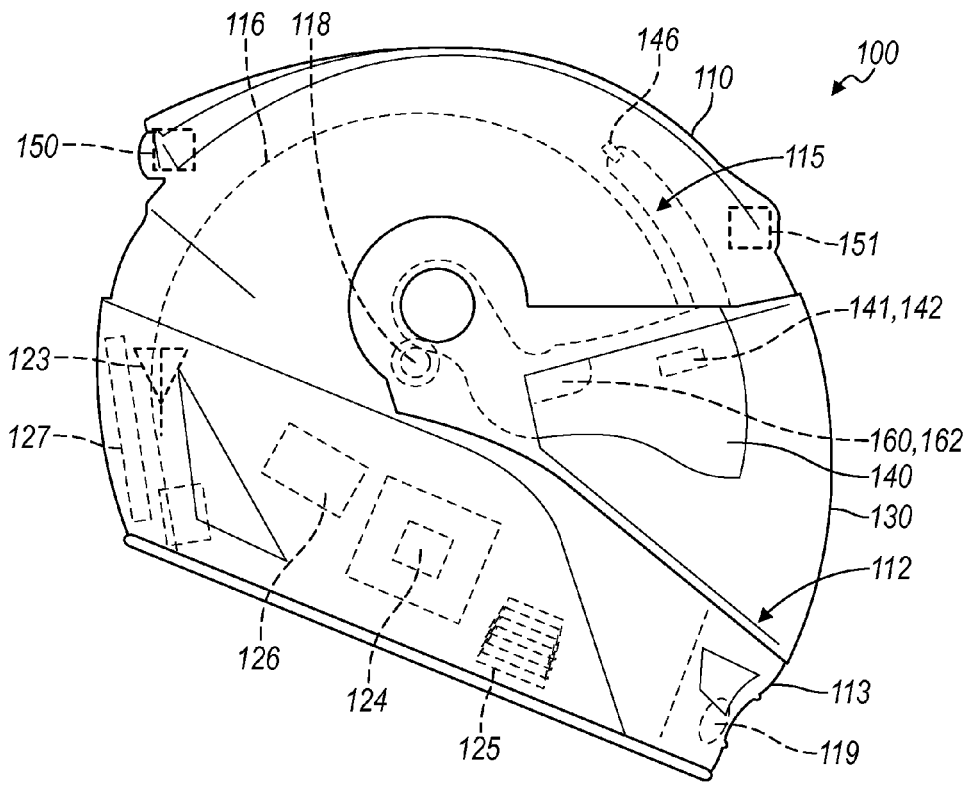
FIG. 5 is a flowchart representation of one variation of the helmet system.

In this variation, the shell 110 can also define one or more speaker receptacles, a microphone receptacle, one or more projector receptacles, a secondary visor 140 receptacle 115, etc. electrically coupled to the fairing 120 via the wiring harness 117, as shown in FIGS. 4 and 5; and the user can selectively install and remove a speaker 118, a microphone 119, a projector, and/or a secondary visor 140, etc. over time to customize functions supported by the helmet system 100.

Furthermore, in this variation, the fairing 120 can form a spoiler (or cooperates with an existing spoiler integrated into helmet shell) to reduce lift and/or wind buffeting of the helmet system 100 and to reduce noise at high speed.

1.4 Primary Visor

The primary visor 130 of the helmet system 100 is coupled to the shell 110 and is transiently arranged over the aperture 112. Generally, the primary visor 130 functions to cover, close, and/or seal the aperture 112 of the shell 110 when lowered and can be raised or removed from the aperture 112. The primary visor 130 can include a polarized polymer screen arranged on the outside of the shell 110 and configured to pivot and/or translate over the aperture 112. For example, the primary visor 130 can include a transparent face shield pivotably coupled to the shell 110 by a hinge mechanism at each outer lateral side of the shell 110. Alternatively, the primary visor 130 can be suspended from the anterior end (i.e., the front) of the shell 110 and can be "flipped" or pivoted between a lowered position and a raised position. Yet alternatively, the primary visor 130 can include a set of goggles worn over the aperture 112 and over the secondary visor 140 and connected to the shell 110 by a strap (e.g., an adjustable elastic strap).

The primary visor 130 can also include a transparent (or translucent) region and an integrated chin guard extending from the transparent region such that, when the primary visor 130 is closed over the aperture 112, the integrated chin guard cooperates with the shell 110 to form a rigid chin bar 113. The primary visor 130 and the shell 110 can thus cooperate to define a modular helmet.

However, the primary visor 130 can be of any other geometry, can be of any other material, and can couple to the shell 110 in any other suitable way.

1.5 Camera

The camera 150 of the helmet system 100 is arranged on the shell 110 and defines a field of view opposite the aperture 112. Generally, the camera 150 functions to capture a sequence of digital photographic images (e.g., video frames) of a field behind the helmet system 100 (and therefore behind the user).

The camera 150 can include a charge coupled device (CCD), an active-pixel sensor (APS), a digital camera, or any other suitable type of optical sensor. The camera 150 can also include a wide-angle (e.g., fisheye) lens that extends the field of view of the camera, such as to a view angle of approximately 170°. In this implementation, the helmet system 100 can dewarp a video frame captured by the camera, crop a region of interest from the dewarped video frame, and then project the region of interest onto the secondary visor 140, as described below. Alternatively, the helmet system 100 can include multiple cameras (or multiple optical sensors) defining fields of view extending outwardly from the posterior end of the shell 110. In this implementation, the helmet system 100 can stitch multiple video frames captured by the set of cameras during a single sampling period into a single composite frame, crop a region of interest from the composite frame, and then project the region of interest onto the secondary visor 140. Alternatively, in the foregoing implementation, the helmet system 100 can select a particular video frame from video frames captured by the set of cameras within a single sampling period—such as based on the user's current riding position or a current pitch angle of the helmet system 100—and display all or a cropped region of the particular video frame on the secondary visor 140.

In one variation, the helmet system 100 includes a forward-facing camera 151 mounted on the shell 110 and defining a field of view extending outwardly from the anterior end of the shell 110. In this variation, the (rear-facing) camera and the forward-facing camera 151 can be of a similar sensor type. Alternatively, in this variation, the forward-facing camera 151 can capture video frames at a first resolution, and the rear-facing camera 150 can capture video frames a second resolution less than the first resolution; thus, the helmet system 100 can record action video with the forward-facing camera 151 for asynchronous consumption by the user through an external display, and the helmet system 100 can render forms of video frames captured by the rear-facing camera 150 on the secondary visor 140 for real-time consumption by the user at the helmet system 100. In this variation, the helmet system 100 can also render forms of video frames captured by the forward-facing camera 151 on the secondary visor 140, such as under certain lighting or ambient conditions. For example, during low-light conditions (e.g., at dusk and at night) the helmet system 100 can enhance video frames captured by the forward-facing camera 151 and project these images on the secondary visor 140 (in addition to or in replacement of video frames from the rear-facing camera iso) to artificially improve the user's vision of a field ahead of the user during low-light conditions. Similarly, the helmet system 100 can include a primary forward-facing camera 151 and a second forward-facing optical sensor (e.g., a thermal sensor), and the helmet system 100 can record action frames with the primary forward-facing camera 151 for asynchronous consumption and can render frames from the second forward-facing optical sensor on the secondary visor 140 until particular conditions (e.g., a night, after dusk) in real-time to artificially improve the user's vision of a field ahead of the user.

1.6 Combiner System

In one variation of the helmet system 100, the secondary visor 140 and the projection system 160 cooperate to form a combiner-type eyes-up display system. In this variation, the secondary visor 140 can be arranged between the aperture 112 and the interior volume 111, can include an elongated translucent member 143 suspended from the shell 110, and can define a first discrete reflective region 141 on a right side of the elongated translucent member 143 and a second discrete reflective region 142 on a left side of the elongated translucent member 143. Furthermore, in this variation, the projection system 160 can project an image onto the first discrete reflective region 141 and onto the second discrete reflective region 142, and the secondary visor 140 can reflect the image toward the interior volume in of the shell 110. Generally, in this variation, the projection system 160 projects an image—through air—toward a reflective (or "active") region of the secondary visor 140, and the reflective region of the secondary visor 140 reflects the incident light projected from the projection system 160 toward the eye(s) of the user.

In this variation, the secondary visor 140 defines a translucent (or transparent) member including a reflective region that resolves a projected image into the user's eyes. For example, translucent member can define a broad planar face including a left reflective region and a right reflective region (or "optical elements"), the left and right reflective regions exhibiting a first transparency (e.g., 70% transparency) and the remainder of the broad planar face exhibiting a second transparency (e.g., ~99%) greater than the first transparency. Thus, the user may see through secondary visor 140—including the left and right reflective regions—when the projection system 160 is powered off or in standby mode. The user may also see through areas of the left and right regions of the secondary visor 140 on which a projected image is null, such as when the projection system 160 projects numerical telemetry data onto a subregion of the right reflective region but the remainder of the right reflective region is empty of an incident image. Furthermore, when the projection system 160 projects an image onto the left and right reflective regions, content of the image may appear translucent (i.e., partially transparent), thereby preserving visual access to the field ahead of the user.

In this variation, the secondary visor 140 can include a planar polymer panel including a discrete internal grating structure defining a reflective region. Thus, when the projection system 160 projects an image onto the grating structure, the grating structure can reflect incident light toward the interior volume in of the shell 110 (e.g., toward the user's eyes) while permitting ambient light outside of the helmet system 100 to pass through the secondary visor 140 to the user's eyes. In this implementation, the planar polymer panel can also include two discrete internal grating structures, including a first grating structure aligned with the user's right eye and a second grating structure aligned with the user's left eye, and the planar polymer panel can be substantially transparent (e.g., exclude a grating structure)

outside of the first and second grating structures defining the first (right) and second (left) reflective regions of the secondary visor 140. The secondary visor 140 can alternatively define a curvilinear profile, and the projection system 160 can process (e.g., distort) an image projected onto the secondary visor 140 to compensate for the curvilinear profile of the secondary visor 140.

The secondary visor 140 can also define an edge profile about a perimeter of the elongated translucent member 143 that limits optical aberration within the user's field of view about the perimeter of the secondary visor 140. For example, the secondary visor 140 can define a beveled edge, a fileted edge, or a serrated edge about the perimeter of the elongated translucent member 143. However, in this variation, the secondary visor 140 can define any other geometry, material, optical element, or edge profile.

Figure 2:
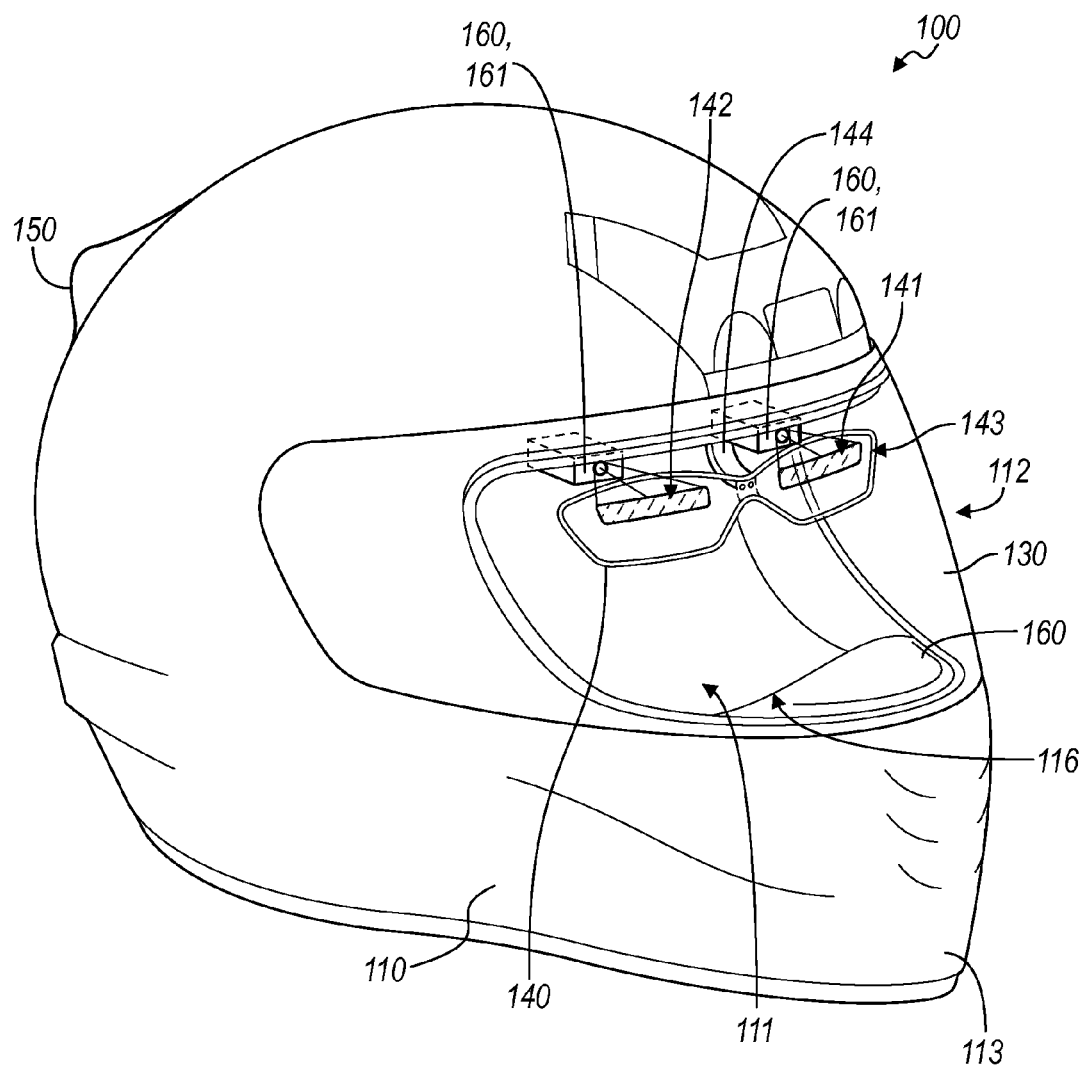
FIG. 2 is a schematic representation of one variation of the helmet system.

In this variation, the projection system 160 includes a projector that projects a sequence of frames (e.g., color images)—through air—onto the secondary visor 140. Thus, in this variation, the projector of the projection system 160 is remote from secondary visor 140. In one implementation in which the shell 110 defines a chin bar 113, the projector is arranged within the chin bar 113 below the secondary visor 140 and projects images upward onto the reflective regions of the secondary visor 140, as shown in FIG. 1. In this implementation, a single projector can project images on the first and second (e.g., right and left) reflective regions of the secondary display. Alternatively, the projection system 160 can include a first projector arranged in the chin bar 113 and dedicated to illuminating the first reflective region of the secondary visor 140, and the projection system 160 can include a second projector adjacent the first projector in the chin bar 113 and dedicated to illuminating the second reflective region of the secondary visor 140. In another implementation, the projection system 160 can include one or more projector(s) arranged overhead the secondary visor 140—such as in a forehead region of the shell 110 or centered between the user's eyes and immediately ahead of the bridge of the user's nose—and similarly projecting an image downward onto the secondary visor 140, as shown in FIG. 2. For example, the projector(s) can be mounted on, coupled to, or integrated into the strut 144 (described above) that extends into the interior volume in of the shell 110 to support the secondary visor 140. In another example: the shell can include a projection bar adjacent and above the aperture; and the projection system can include a first projector and a second projector supported by the projection bar, wherein the first projector is aligned with and projects a first instance of an image onto the first reflective region, and wherein the second projector is aligned with and projects a second instance of the image onto the second reflective region. Yet alternatively, the projection system 160 can include a first projector arranged in the interior volume in of the shell 110 adjacent the user's right temple and a second projector arranged in the interior volume in of the shell 110 adjacent the user's left temple; in this implementation, the first (i.e., right) projector can project an image onto the first (e.g., right) reflective region of the secondary visor 140, and the second (i.e., left) projector can simultaneously project an image onto the second (e.g., left) reflective region of the secondary visor 140, or vice versa. However, the projection system 160 can include any other number of projectors arranged in any other position or orientation within the helmet system 100.

In this variation, the projection system 160 can project a series of monoscopic frames onto the discrete reflective regions of the secondary visor 140. In particular, the projection system 160 can project a first instance of a first image onto the first discrete reflective region 141 of the secondary visor 140 and project a second instance of the first image—identical to the first instance of the first image aside from focusing, scaling, orientation, and/or position adjustments specific to the second side of the secondary visor 140—onto the second discrete reflective region 142 (substantially) simultaneously at a first time. After a refresh period, the projection system 160 then projects a first instance of a second image onto the first discrete reflective region 141 and projects a second instance of the second image—identical to the first instance of the second image aside from focusing, scaling, orientation, and/or position adjustments specific to the second side of the secondary visor 140—onto the second discrete reflective region 142 (substantially) simultaneously at a second, succeeding time. Alternatively, the projection system 160 can project stereoscopic frames (i.e., different but paired images) onto the secondary visor 140 for each sequential refresh period during use of the helmet system 100, such as to project a three-dimensional augmented-reality overlay onto the secondary visor. For example, in the implementation of the helmet system 100 that includes a left-rear-facing camera 150 and a right-rear-facing camera 150, a first projector in the projection system 160 can project a form of an image captured by the right-rear-facing camera 150 at a first time onto the first (e.g., right) reflective region of the secondary visor 140, and a second projector in the projection system 160 (or the first projector) can project a form of an image captured by the left-rear-facing camera 150 at approximately the first time onto the second (e.g., left) reflective region of the secondary visor 140 to provide the user with a three-dimensional virtual view of a scene behind the user (e.g., behind the posterior end of the helmet system 100).

Figure 6:
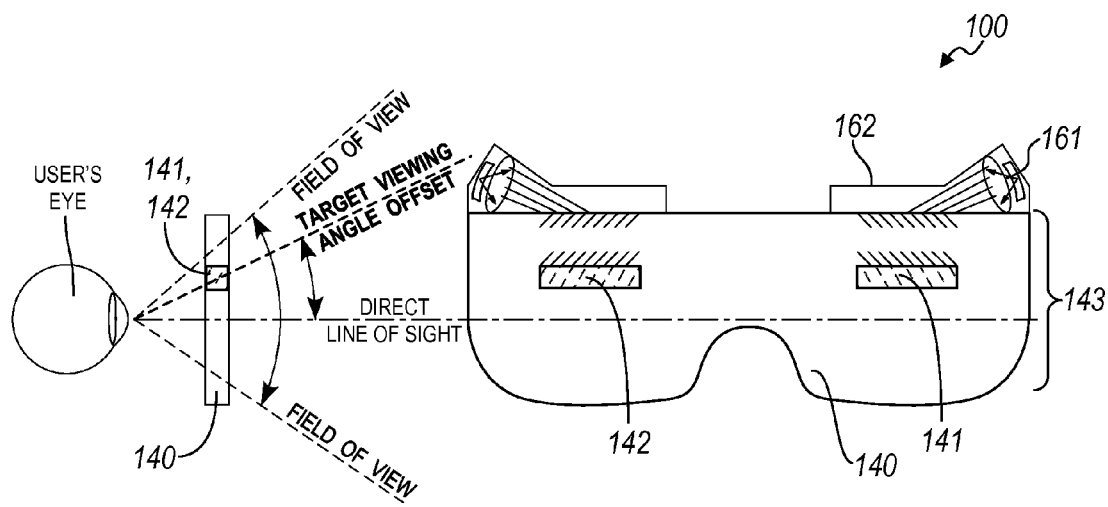
FIG. 6 is a schematic representation of one variation of the helmet system.

Therefore, in the foregoing variation, the secondary visor 140 can define one or more reflective regions within the user's direct field of view but outside of the user's direct line of sight when looking outwardly through the aperture 112, as shown in FIG. 6. The projection system 160 can thus project a pair of monoscopic frames onto the reflective regions of the secondary visor 140 such that the pair of monoscopic frames appears—to the user—as a single convergent image in focus at a distance ahead of the user. The user can thus glance slightly upward to access visual content from the convergent image during use. However, in this variation, the secondary visor 140 and the projection system 160 can cooperate in any other way to display monoscopic or stereoscopic images onto the first and secondary reflective regions for visual consumption by the user.

1.7 Waveguide System

In another variation of the helmet system 100, the secondary visor 140 and the projection system 160 cooperate to form a waveguide-type eyes-up display system. In one implementation of this variation, the optical element of the secondary visor 140 includes diffraction optics. In this implementation, the projection system 160 includes a waveguide 162 adjacent the secondary visor 140 and a projector that projects an image in the form of collimated light into the waveguide 162. The waveguide 162 includes a first set of deep slanted diffraction gratings that in-couple the collimated light, and the waveguide 162 guides the light through an edge of the secondary visor 140 and toward a second set of deep slanted diffraction gratings (i.e., the optical element). The second set of deep slanted diffraction gratings out-couples and reflects this light toward the interior volume in of the shell 110 (e.g., toward the user's eyes).

In a similar implementation, the optical element of the secondary visor 140 includes holographic optics. As above, the projection system 160 includes a waveguide 162 adjacent the secondary visor 140 and a projector that projects an image in the form of collimated red, green, and blue light into the waveguide 162. The waveguide 162 includes a first set of holographic elements (e.g., a first red holographic element that reflects red light, a first green holographic element that reflects green light, and a first blue holographic element that reflects blue light) that in-couple the collimated light, and the waveguide 162 guides the light through an edge of the secondary visor 140 and toward a second set of holographic elements (e.g., a second red holographic element that reflects red light, a second green holographic element that reflects green light, and a second blue holographic element that reflects blue light). The second set of holographic elements out-couples and reflects this light toward the interior volume in of the shell 110. In this implementation, the holographic optical elements can include sub-sections that can be selectively switched on and off to step or sequence an image set across the waveguide.

In another implementation, the optical element of the secondary visor 140 includes polarized optics. As above, the projection system 160 includes a waveguide 162 adjacent the secondary visor 140 and a projector that projects an image into the waveguide 162. The waveguide 162 guides light output from the projector into an edge of the secondary visor 140 and toward a set of polarized reflectors embedded into or arranged over a surface of the translucent body of the secondary visor 140. The polarized reflectors then reflect incident light toward the interior volume in of the shell no. In this implementation, the secondary visor 140 can include a transparent substrate (e.g., an elongated transparent glass member) and a series of multi-layer polarized coatings applied over the transparent substrate to define a discrete optical element (e.g., a discrete active region, a discrete reflective region).

In yet another implementation, the optical element of the secondary visor 140 includes reflective optics. In this implementation, the projection system 160 includes a projector (e.g., a micro display) and a waveguide 162 that communicates light from the projector into the secondary visor 140 via a set of prisms selectively coated with a semi-reflective material. The secondary visor 140 includes a semi-transparent, semi-reflective mirrored structure (the optical element) internal (i.e., integrated inside the body of) the transparent substrate of the secondary visor 140, and the semi-reflective mirrored structure reflects incident light from the waveguide 162 toward the interior volume in of the shell 110 (e.g., into the user's eyes). In one example implementation, the projection system includes a projector that outputs visible light within discrete, limited wavelength bands, such as one discrete band between 3 nanometers and 15 nanometers in width at half of maximum intensity for each illumination source, including a first band centered between 610-640 nanometers for red light, a second band between 513-530 nanometers for green light, and a third band centered between 440-470 nanometers for blue light. In this example implementation, a reflective region of the secondary visor includes a first coating exhibiting relatively high reflective brightness (e.g., greater than 10% reflective brightness) for a first particular wavelength of red light (e.g., 617 nanometers) or for a first limited range of wavelengths (e.g., 615-620 nanometers) but a relatively low reflective brightness (e.g., less than 1%) for other wavelengths of visible light outside the first particular wavelength or outside the first limited range of wavelengths such that the first coating on the reflective region of the secondary visor reflects red light output from the projector toward the user's eye(s) but passes substantially all other ambient light—originating outside of the helmet system—on to the user's eye(s). Similarly, the reflective region of the secondary visor can include a second coating exhibiting relatively high reflective brightness for a second particular wavelength of green light (e.g., 515.5 nanometers) or for a second limited range of wavelengths (e.g., 513-517 nanometers) but a relatively low reflective brightness for other wavelengths of visible light outside this second particular wavelength or outside the second limited range of wavelengths such that the second coating on the reflective region of the secondary visor reflects green light output from the projector toward the user's eye(s) but passes substantially all other ambient light on to the user's eye(s). Furthermore, the reflective region of the secondary visor can include a third coating exhibiting relatively high reflective brightness for a third particular wavelength of blue light (e.g., 460 nanometers) or for a third limited range of wavelengths (e.g., 458-462 nanometers) but a relatively low reflective brightness for other wavelengths of visible light outside this third particular wavelength or outside the third limited range of wavelengths such that the third coating on the reflective region of the secondary visor reflects blue light output from the projector toward the user's eye(s) but passes substantially all other ambient light on to the user's eye(s). The secondary visor can therefore include one or more coatings exhibiting optical properties that are matched to light output characteristics of the projection system.

In the foregoing example implementation, each reflective region on the secondary visor can include a series of coatings that are relatively-highly-reflective to light output by the projection system but that are relatively transparent to wavelengths of visible light outside the limited wavelength bands supported by the projection system. Thus, the secondary visor can appear to the user as nearly-uniformly transparent (or nearly-uniformly translucent) across a range of lighting conditions while yielding both relatively high brightness for ambient light communicated from outside of the helmet system to the user's eyes and relatively high brightness for projected light output by the internal projection system and projected into the user's eyes by the secondary visor. For example, the secondary visor can define both a reflective region and a peripheral—wherein the reflective region includes a multi-layer coating that is relatively highly reflective to select narrow wavelength bands, and wherein the peripheral region is physically adjacent (e.g., surrounding) the reflective region but more uniformly reflective across the spectrum of visible light—such that the reflective region and the peripheral region appear substantially similarly transparent to the user across a range of ambient lighting conditions.

Alternatively, the secondary visor can include a reflective region including a broadband reflective coating—applied to a surface of or integrated into a structure of the secondary visor—exhibiting a first reflective brightnesses (e.g., 40%, substantially uniformly across the visible spectrum) exceeding a second reflective brightness of the peripheral region of the secondary visor (e.g., less than 1% across the visible spectrum) for a wider range of wavelengths of visual light, such as from 390 nanometers to 710 nanometers. The secondary visor can also include a diffraction grating or any other suitable optical element, coating, or liner to achieve any of the foregoing characteristics in one or more reflective regions.

In the foregoing implementations, the waveguide 162 and the secondary visor 140 can be physically coextensive. For example, the secondary visor 140 can include a series of internal optical elements (e.g., polarized reflectors, semi-reflective mirrors, holographic elements, etc.) embedded or integrated into a transparent substrate (e.g., the elongated transparent substrate); the projection system 160 can include a projector that projects light directly into an internal waveguide thus defined by the secondary visor 140, and the secondary visor 140 can guide light from the projector internally to a set of optical elements that out-couple incident light to the user's eyes. Alternatively, the waveguide 162 and the secondary visor 140 can be discrete components within the helmet system 100, wherein the waveguide 162 is interposed between the secondary visor 140 and a remote projector of the projection system 160. Thus, as described below, the waveguide 162 and/or the projector can be separable from the secondary visor 140.

In this variation, the secondary visor 140 can include one or more optical elements, such as a single optical element on the right side of the secondary visor 140 (and arranged in the field of view of the user's right eye), or such as a right optical element and a left optical element arranged in the field of view of the user's right eye and in the field of view of the user's left eye, respectively. The projection system 160 can contain a single projector that projects a first instance of a monoscopic image onto the right optical element and a second instance of the monoscopic image (i.e., a duplicate of the first instance) onto the left optical element simultaneously. For example, the projection system 160 can align the first and second instances of the monoscopic image laterally into a single frame and project the frame through a split waveguide that transmits the right half of the frame to the right optical element and the left half of the frame to the left optical element. In this example, the projector and the split waveguide can be arranged overhead (or under) the secondary visor 140. Alternatively, the projection system 160 can include a right projector and a right waveguide dedicated to projecting images onto the right optical element of the secondary visor 140 and a left projector and a left waveguide dedicated to projecting images onto the left optical element of the secondary visor 140, as shown in FIG. 6. For example: the secondary visor 140 can extend vertically above the user's upper field of view; and the right projector, the right waveguide, the left projector, and the left waveguide can be arranged overhead (or below) the secondary visor 140 and therefore outside of the user's field of view. In a similar implementation, the secondary visor 140 can extend laterally across the aperture 112 and beyond the user's lateral field of view, and the right projector and the right waveguide can be arranged to the right of the secondary visor 140 and outside of the user's right-lateral field of view, and the left projector and the left waveguide 162 can be arranged to the left of the secondary visor 140 and outside of the user's left-lateral field of view.

1.8 Fixed Secondary Visor 140

In one implementation, the helmet system 100 also includes a strut 144 extending from the shell 110 into the interior volume in and supporting the secondary visor 140. For example, the helmet system 100 can include a rigid strut extending from the inner surface of the shell 110 proximal the top (e.g., dorsal side) of the shell 110 behind the upper edge of the aperture 112 and extending downward into the user's field of view, and the secondary visor 140 can be fastened to the distal end of the strut 144 and extending laterally across the user's field of view. In this example, the secondary visor 140 can include: a right window of a first height and defining the first discrete reflective region 141; a left window of the first height and defining the second discrete reflective region 142; and a neck of a second height less than the first height, interposed between and supporting the right window and the left window, and suspended from the distal end of the strut 144, as shown in FIGS. 1 and 4. In this implementation, the strut 144 can be substantially rigid (e.g., a composite or metallic structure), rigidly coupled to the shell 110 (e.g., via an adhesive or threaded fastener) and can rigidly support the secondary visor 140. Alternatively, the strut 144 can be coupled to the shell 110 by an adjustable linkage and/or coupled to the secondary visor 140 by an adjustable linkage, and the user can mechanically adjust a position of the secondary visor 140—and therefore a perceived position of an image viewed through the secondary visor 140 when projected on the secondary visor 140—by manipulating the adjustable linkage(s) to adjust the position of the strut 144 and/or the secondary visor 140 relative to the shell 110. For example, the secondary visor 140 can be coupled to the strut 144 by a friction ball joint, and the strut 144 can include a sliding link fastened by a thumbscrew; the user can thus move the secondary visor 140 vertically within the aperture 112 of the shell 110 to set the secondary visor 140 in front of his eyes, and the user can pivot the secondary visor 140 to align an image reflected off of the secondary visor 140 with his eyes. However, the secondary visor 140 can be coupled to the strut 144, and the strut 144 can be coupled to the shell 110 in any other way.

Alternatively, the secondary visor 140 and the strut 144 can be static, and the projection system 160 can adjust a vertical position, horizontal position, keystone setting, scale, etc. of an image in order to compensate for a real position of the user's eyes relative to the secondary visor 140 when wearing the helmet system 100.

Furthermore, the secondary visor 140 can be damped against the strut 144 (or against the visor)—such as by a damper 145—to limit oscillation of the secondary visor 140 during use. For example, the helmet system 100 can include a rubber washer (e.g., o-ring), silicone sheath, or other passive damping element between the strut 144 and the secondary visor 140 (or between the strut 144 and the shell 110) that damps oscillatory motion of the secondary visor 140 during use, thereby limiting fluctuations in perceived positions of content (e.g., rear field images, telemetry data) projected on the reflective regions of the secondary visor 140. In another example, the helmet system 100 includes a hydraulic or pneumatic tube damper extending from the secondary visor 140 to the strut 144 or from the strut 144 directly to the shell 110. In this implementation, the type, size, and/or material (e.g., durometer) of the damping element can be selected based on an application specific to the helmet system 100. For example, for a helmet system designated for a sportbike with an engine capable of reaching speeds of 11,000 revolutions per minutes, the damping element can be selected to damp a target oscillation frequency of 90 Hz (i.e., roughly the center of the engine speed range of the sportbike); and a helmet system designated for an American cruiser motorcycle with an engine capable of reaching speeds of 5,000 revolutions per minute, the damping element can be selected to damp a target oscillation frequency of 40 Hz (i.e., roughly the center of the engine speed range of the cruiser). In another example, a helmet system designated for skiing, the damping element can be selected to damp a target oscillation frequency corresponding to a high-amplitude oscillating input common to skiing (e.g., 10 Hz for an undulating downhill ski route). Therefore, as in these examples, the damping element can be selected (e.g., sized, configured) to damp oscillation of the secondary visor 140 in the event of a relatively high-amplitude oscillation input common to the application for which the helmet system 100 is designated.

In the foregoing implementation, the damping element and the strut 144 can be arranged within the interior volume in of the shell 110 such that the damping element and the strut 144 are (predominantly) outside a perimeter of the user's field of view (or above the user's eyeline) when looking through the aperture 112 and beyond the helmet system 100.

1.9 Retractable Secondary Visor 140

In one variation, the secondary visor 140: includes an optical element, is operable between a retracted position and an active position, is arranged between a dorsal region of the shell 110 and the interior volume 111 in the retracted position, and is arranged between the aperture 112 and the interior volume 111 in the active position. Furthermore, in this variation, the projection system 160 transitions from a standby mode to an active mode in response to transition of the secondary visor 140 from the retracted position to the active position and projects an image toward the optical element in the active mode, and the optical element reflects the image toward the interior volume in of the shell 110.

Generally, in this variation, the secondary visor 140 can be retracted from the aperture, such as independently of the primary visor 130. In particular, the secondary visor 140 can be curved in one or more perpendicular cross-sections (i.e., define an arciform profile) to match a visor receptacle 115 within the interior volume 111 of the shell 110, within the shell 110, or over an exterior surface of the shell 110. For example, the secondary visor 140 can include a translucent wraparound visor defining a boundary that extends beyond the user's field of view (e.g., proximal or outside of a typical human's peripheral field of view) and curved in two planes to fit between the shell 110 and a comfort lining 116 inside the shell 110 when the secondary visor 140 is retracted, as shown in FIG. 5. Similarly, the shell 110 can include an inner shell structure and an outer shell structure filled with an impact-absorbing foam, as described above, and the inner shell structure and the outer shell structure can cooperate to define a cavity over the aperture 112; the secondary visor 140 can thus be retracted into the cavity in the retracted setting and extend into position over or adjacent the aperture 112 in the active setting. Alternatively, the secondary visor 140 can be configured to retract into a visor receptacle 115 between the comfort lining 116 and the top of the user's head or between the comfort lining 116 and the user's forehead. Yet alternatively, the exterior of shell can define a recess above the aperture 112, the helmet system 100 can include a cover (e.g., a polymer cover plate) over the recess, and the secondary visor 140 can retract into the recess in the retracted position. However, in this variation, the helmet system 100 can define a recess, receptacle, or pocket, etc. configured to house the secondary visor 140 in the retracted setting.

Thus, in this variation, the projection system 160 can distort an image—before projecting the image through the secondary visor 140—to compensate for the arciform profile of the secondary visor 140. Alternatively, in this variation, the secondary visor 140 can define a substantially planar translucent member—as described above—sized to retract into an elongated pocket above (or below) the aperture 112.

In this variation, the secondary visor 140 can be pivotably coupled to the shell 110. For example, the secondary visor 140 can be coupled to the shell 110 via a friction hinge on each side of the secondary visor 140 and can pivot between the retracted position above (or below) the aperture 112 and the active position within (or over, behind) the aperture 112. The secondary visor 140 can additionally or alternatively translate between the retracted and active positions. For example, the secondary visor 140 can be coupled to the shell 110 on each lateral side by a four-bar linkage. However, the secondary visor 140 can be coupled to the shell 110 in any other way or with any other suitable linkage.

The helmet system 100 can further include a latch 147 coupled to the secondary visor and extending to an exterior surface of the shell 110. A user can thus access and manipulate the latch 147 manually from outside the shell 110 to shift the secondary visor 140 between the active and retracted positions. Alternatively, the helmet system 100 can include an (electromechanical) actuator that moves the secondary visor 140 between the retracted and active positions, such as in response to selection of an input region 122 on an exterior surface of the shell 110 (or on the fairing 120, as shown in FIG. 3) or in response to an input on a mobile computing device (e.g., smartphone) wirelessly connected to the helmet system 100. The helmet system 100 can also include a position sensor coupled to the secondary visor 140, and the projection system 160 can transition between the standby mode and the active mode based on an output of the position sensor. For example, the position sensor can include a limit switch 146 that changes state when the secondary visor 140 enters the active position within (or over, behind) the aperture 112; the projection system 160 can shut down or enter the standby mode when an output of the limit switch 146 indicates that the secondary visor 140 is not in the active position, and the projection system 160 can power on (and project an image onto the secondary visor 140) when an output of the limit switch 146 indicates that the secondary visor 140 is in the active position.

In one implementation, the projection system 160 includes a projector 161 rigidly coupled to the secondary visor 140, wherein the projector 161 transitions between the retracted position and the active position in-unit with the secondary visor 140. For example, the projection system 160 can include: a projector 161 and a waveguide 162 mounted to and arranged vertically over the secondary visor 140; and a display driver 163 arranged within the shell 110 or within the fairing 120 and coupled to the projector 161 via a wiring harness 117 passing through a hinge that couples the secondary visor 140 to the shell 110. In this example, the projector 161 and the waveguide 162 can move in-unit with the secondary visor 140 as the secondary visor 140 transitions between the retracted position and the active position.

Alternatively, the projection system 160 can include a projector 161 separable from the secondary visor 140, wherein the secondary visor 140 rotates and/or translates relative to the projector 161 between the retracted and active positions. In one example, the projection system 160 includes a projector 161 rigidly supported by the shell 110 adjacent a lateral side (e.g., the right side) of the aperture 112, separated from the secondary visor 140 in the retracted setting, and aligned with and projecting an image through the secondary visor 140 to the optical element (via a corresponding waveguide 162) in the active position. In this example, the projection system 160 can include a right projector and a right waveguide adjacent the right side of the secondary visor 140 and a left projector and a left waveguide 162 adjacent the left side of the secondary visor 140, when the secondary visor 140 pivots into the active position between the right and left waveguides to receive images projected from the right and left projectors, respectively. In another example in which the shell 110 defines a chin bar 113, the projection system 160 can include a projector 161 and a waveguide 162 in the chin bar 113, wherein the waveguide 162 physically contacts a bottom edge of the secondary visor 140 and communicates light into the secondary visor 140 toward the optical element(s) when the secondary visor 140 is in the active position, as shown in FIG. 3; in this example, the waveguide 162 is separated from the secondary visor 140 in the retracted position, and the projection system 160 shuts down or enters the standby mode accordingly. In this implementation, the secondary visor 140 can define a mating surface that engages a location feature defined by the waveguide 162, the projector 161, and/or the shell 110 to locate the secondary visor 140 relative to the waveguide 162 and/or to the projector 161 in the active position. For example, the waveguide 162 and the projector 161 can be rigidly mounted to the shell 110, the shell 110 can define a locating bore proximal each lower corner of the aperture 112, and the visor can define a locating pin proximal each lower outer corner and configured to engage an adjacent locating bore in the active position, wherein a hinge system supporting the secondary visor 140, the locating pins, and the locating bores cooperate to repeatably align the secondary visor 140 with the projector(s) and/or with the waveguide(s)). However, in this implementation, the helmet system 100 can include any other features or mechanisms to repeatably locate the secondary visor 140 relative to the projection system 160 between transitions from the retracted position to the active position.

1.10 Image Processing

Figure 7:
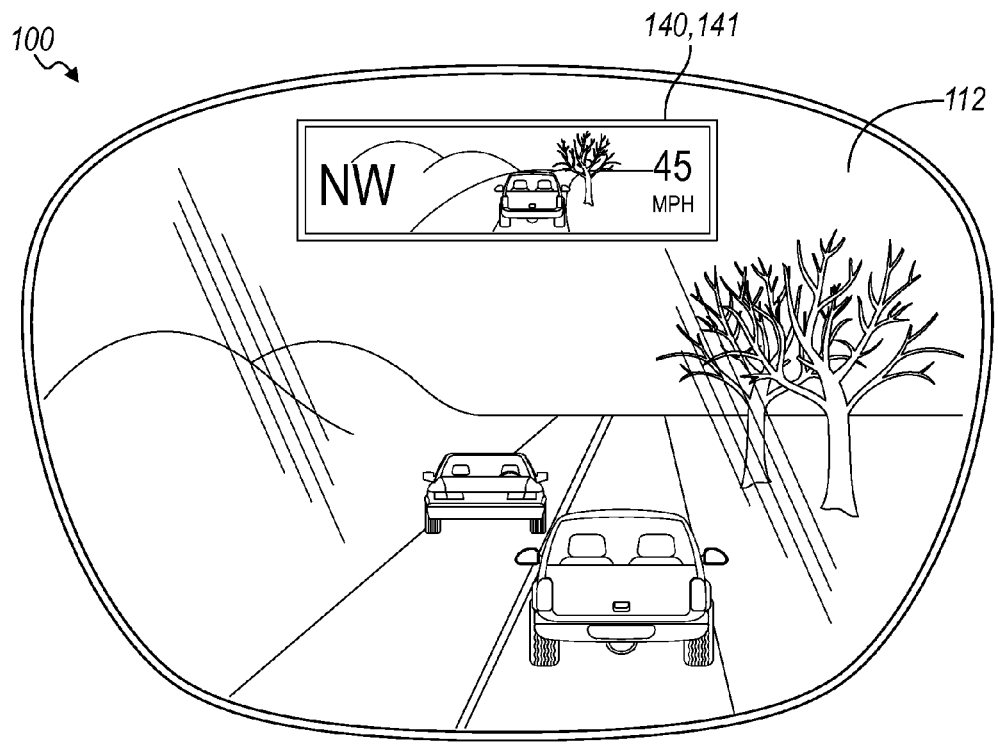
FIG. 7 is a graphical representation of one variation of the helmet system.
Figure 8:
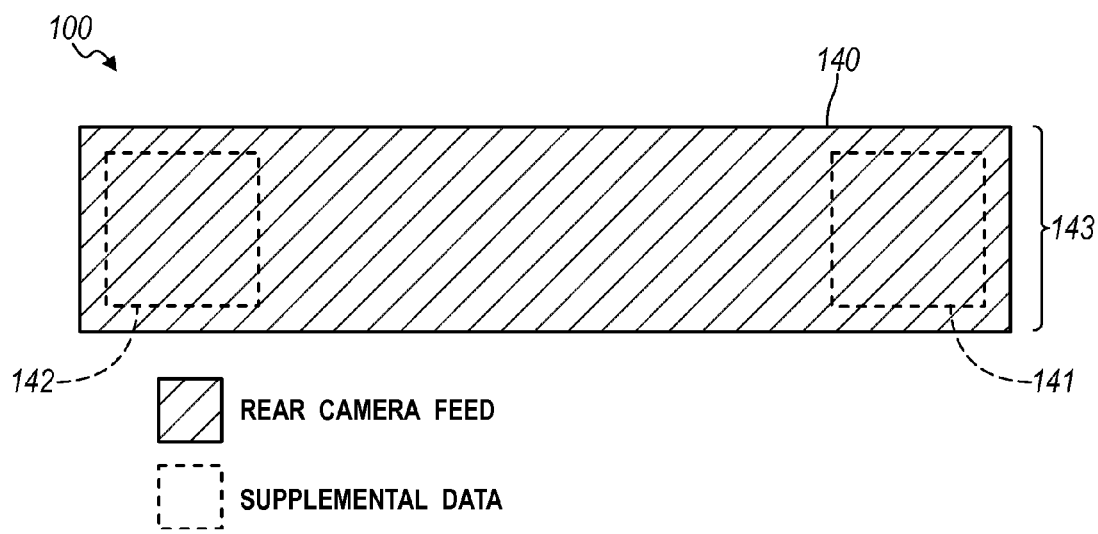
FIG. 8 is a schematic representation of one variation of the helmet system.

The projection system 160 of the helmet system 100 can include a display driver 163 that processes digital frames captured by the rear-facing camera 150, digital frames captured by the forward-facing camera 151, data collected from integrated sensors, and/or data received from an external computing device (e.g., a mobile computing device, a wireless-enabled motorcycle) into frames that are then projected onto the secondary visor 140 for visual consumption by the user. In particular, the projection system 160 cooperates within the secondary visor 140 to display a live video stream of a field behind the user (i.e., behind the helmet system 100)—output by the camera 150—and can augment this live video feed with live telemetry data (e.g., road speed, direction), live systems data (e.g., oil pressure, engine speed, fuel or battery level, range), and/or navigation data, etc. in real-time, as shown in FIGS. 7 and 8. Thus, when the user is looking straight-ahead, the projection system 160 can project a live video stream of a field immediately behind the user; the user can then rotate his head to his left (and raise his gaze slightly to the reflective regions on the secondary visor 140) to view the field behind and to the right of the user, the user can rotate his head to his right to view the field behind and to the left of the user, and the user can look forward and tilt his head upward to view the field behind and below the user, such as a scene including the tail of the motorcycle the user is riding and road immediately behind the motorcycle.

In one implementation in which the helmet system 100 includes a single rear-facing camera with a wide-angle lens, the projection system 160 can dewarp or "flatten" video frames captured by the camera 150 during use to produce rectified digital frames. Alternatively, in another implementation in which the helmet system 100 includes multiple rear-facing cameras, in which the helmet system 100 includes a single rear-facing camera 150 with a wide-angle lens, the projection system 160 can stitch multiple frames captured by the cameras in a single sampling period into a single (flat) rectified digital frame. The projection system 160 applies a crop area to a rectified digital frame—substantially in real-time—to generate an image and then mirrors the image horizontally (such that the field to the rear left of user is displaying on the left side of the secondary visor 140 and such that the field to the rear right of user is shown on the right side of the secondary visor 140). The projection system 160 can also modify (e.g., warp) the image virtually to compensate for a shape of the secondary visor 140, arrangement of optical elements in the secondary visor 140, image position and keystone preferences for the helmet system 100, etc. before projecting the image onto (or through) the secondary visor 140.

The projection system 160 can apply a dynamic crop area to rectified digital frames (or to video frame) captured by the camera. For example, the projection system 160 can set the vertical position of a crop area within a rectified digital frame based on the user's riding position. In this example, while sitting on or riding a motorcycle in a desired riding position—including a desired head position—the user can select an input region 122 on the exterior of the shell 110 or in a native helmet controls application executing on a connected mobile computing device to confirm the riding position. In response to selection of the input region 122, the projection system 160 can record a pitch angle of the helmet system 100 (e.g., by reading an accelerometer or tilt sensor arranged within the helmet system 100, such as within the faring) and then lock the vertical position of the crop area within subsequent video frames based on the pitch angle of the helmet. In this example, the projection system 160 can pass the pitch angle of the helmet through a lookup table or parametric engine to transform the pitch angle of the helmet into a vertical position of the crop area for subsequent rectified digital frames or video frames captured by the camera. In particular, when the user is riding a sportbike in a forward riding position characterized by a negative pitch angle (e.g., approximately −20°) and selects the input region 122 to lock the crop area for the rearview video stream, the projection system 160 can shift the crop area within a video frame toward the vertical center of the video frame. For example, for the video frame 2000 pixels in height, crop area 800 pixels tall, and a measured pitch angle of −20°, the projection system 160 can set the center of the crop area 400 pixels below the center a subsequent series of video frames. Furthermore, when the user is riding a cruiser in an upright riding position characterized by a near-zero pitch angle (e.g., ±2°) and selects the input region 122 to lock the crop area for the rearview video stream, the projection system 160 can shift the crop area within a video frame downward into a lower portion of the video frame. For example, for a measured pitch angle of between −2° and +2°, the projection system 160 can set the vertical center of the crop area at the vertical center of a subsequent series of video frames. The projection system 160 can thus lock the vertical position of the crop area across a sequence of video frames (e.g., a streaming video feed). The projection system 160 can thus enable the user to point his head (and therefore the helmet system 100) upward to view the ground immediately behind the user through the secondary visor 140 and thus enable the user to point his head downward to view the sky immediately behind the user through the secondary visor 140.

The projection system 160 can also float the crop area across video frames output from the camera 150 to preserve the rear field of view displayed on the secondary visor 140 across a range of helmet system pitch angles. For example, the projection system 160 can tag each video frame received from the camera 150 with a pitch angle of the helmet system 100 measured at or around the time the video frame was captured; based on an angular difference between the pitch angle of the helmet and gravity, the projection system 160 can set the vertical position of the crop area within the video frame; crop the video frame to generate an image; and project the image onto the secondary visor 140 substantially in real-time. In this example, the projection system 160 can repeat the process for each consecutive video frame captured by the rear-facing camera 150 such that the rear field of view projected onto the secondary visor 140 is preserved across a range of helmet system pitch angles.

The projection system 160 can also implement the foregoing crop area lock and crop area float implementations selectively, such as based on a mode selected by the user through a region on the shell 110 or through a native helmet controls application executing on a connected mobile computing device. The projection system 160 can also lock the crop area to a reference position within the a sequence of video frames output by the camera, as described above in the crop area lock implementation, but also implement methods and techniques described in the float implementation to make small adjustments to the vertical position of a crop area within a video frame, such as based on outputs of inertial sensors 125 within the helmet system 100, to stabilize displayed images across a video feed. Alternatively, the user can set the crop area lock position and/or crop area float parameters manually, such as based on an input provided by the user through the input region 122 on the shell 110 or through the native helmet controls application. The projection system 160 can implement similar methods and techniques to lock or float the horizontal position of crop areas across a sequence of video frames captured by the rear-facing camera 150.

The projection system 160 can crop video frames into images for projection onto the secondary visor 140 by applying crop area of static dimension and geometry (e.g., 200 pixels square) to video frames—of static dimension and geometry—output from the rear-facing camera 150. Alternatively, the projection system 160 can modify the size and/or shape of the crop area, such as based on a zoom preference selected by the user. The projection system 160 can also compress or resize video frames and/or images for projection onto the secondary visor 140 to achieve alternate zoom levels for the rear field video feed.

Once the projection system 160 transforms a video frame captured by the rear-facing (or other) camera into an image, the projection system 160 prepares the image for display on the secondary visor 140. For example, the projection system 160 can horizontally mirror the image (as described above), stretch the image linearly or arcuately in one or more directions, keystone the image to compensate for optical distortion of light projected from the projector 161 onto (or through) the secondary visor 140, or translate the image vertically or horizontally to achieve a target display position for the image on the secondary visor 140

In one implementation, the projection system 160 dynamically positions the image on the optical element based on the pitch angle of the helmet system 100. Generally, in this implementation, the projection system 160 can estimate a region of the secondary visor 140 coincident the user's direct line of sight based on a pitch angle of the helmet system 100 and a preset standard direct line of sight angle (e.g., 5° below horizontal) or a user-elected direct line of sight angle stored in a display preference on the helmet system 100 or on a connected mobile computing device. In particular, the projection system 160 can: access a model defining a standard preset or user-corrected position of the user's eye within the interior volume in of the shell 110; predict the user's direct (forward) line of sight from the user's eye position within the helmet system 100 based on the elected direct line of site angle; calculate the position of the secondary visor 140 and/or the optical element(s) relative to the user's direct line of sight based on the current pitch angle of the helmet system 100 and a known position and orientation of the secondary visor 140 and/or the optical element(s) within the shell 110; and thus determine a region of the secondary visor 140 and/or the optical element(s) coincident or adjacent the user's direct line of site. The projection system 160 can then shift the vertical position of an image projected onto (or through) the secondary visor 140 to achieve a target viewing angle offset and/or position offset for the image from (e.g., 2° above or below) the user's direct line of sight, as shown in FIG. 6. For example, the projection system 160 can retrieve a target viewing angle offset for images displayed on the secondary visor 140 from a directory of user preferences stored locally on the helmet system 100. Alternatively, the helmet system 100 can include an actuator that automatically adjusts the vertical position and/or the pitch angle of the secondary visor 140 relative to the aperture 112 to achieve the target viewing angle offset for the image displayed on the secondary visor 140. The projection system 160 can repeatedly and dynamically modify image positioning parameters (and/or the real position of the secondary visor 140) substantially in real-time based on the pitch angle (or other measured orientation) of the helmet system 100; the projection system 160 can thus update and apply these image positioning parameters to successive images before projecting these images onto (or through) the secondary visor 140.

In the foregoing implementation, the projection system 160 can horizontally shift (or "pixel shift") an image projected onto the secondary visor based on a manual input entered directly into the helmet system on into a connected device by the user. For example, the projection system can horizontally shift one of a right or left image projected on the secondary visor or horizontally shift both the right and left projected relative to the centerline of the shell based on a manual input into the input region on the shell; to correct for inter-pupil variation of the projected images in a region of the secondary visor 140 coincident the user's direct line of sight, the user can thus select the input region on the helmet system until the a first image projected on the right reflective region and a second image projected on the left reflection region are "seen as one" image. The projection system can then store the positions of the right and left images as default image positions and recall these positions each time the projection system is actuated (and until the default image positions are similarly updated at a later time). In this implementation, the projection system 160 can: access a model defining a standard preset or user-corrected position of the user's eye(s) within the interior volume in of the shell 110; predict the user's direct (forward) line of sight from the user's eye position within the helmet system 100 based on the elected direct line of site angle; calculate the position of the secondary visor 140 and/or the optical element(s) relative to the user's direct line of sight based on the current pitch angle of the helmet system 100 and a known position and orientation of the secondary visor 140 and/or the optical element(s) within the shell 110; and thus determine a region of the secondary visor 140 and/or the optical element(s) coincident or adjacent the user's direct line of site. The projection system 160 can then shift the horizontal position of an image projected onto (or through) the secondary visor 140 to achieve an aligned target viewing position in addition to the offset and/or position offset for the image from (e.g., 2° above or below) the user's direct line of sight, as shown in FIG. 6.

The projection system 160 can also add data from an external device, such as downloaded from a wireless-enabled vehicle (e.g., a motorcycle) or from a smartphone. For example, the helmet system 100 can: download road speed, engine speed, oil pressure, and system warnings substantially in real-time from a motorcycle ridden by the user; download navigation commands and text message data from a smartphone wirelessly-connected to the helmet system 100; and then selectively combine these data with images generated from video frames captured by the rear-facing camera 150 to form composite frames. In this example, the projection system 160 can overlay these external data onto particular subregions of an image to generate a composite image, such as by overlaying heading and navigational data received at a particular instant in time over a top-right corner of the image and by overlaying road speed data on a bottom-left side of the image, the image generated from a video frame recorded at approximately the particular instant in time.

The projection system 160 can also cooperate with the wireless communication module to download a set of image projection settings from an external mobile computing device, such as vertical and horizontal position, keystone, scaling, focus, data overlay, and/or other display parameters. The projection system 160 can then manipulate images according to these parameters before projecting these images onto or through the secondary visor 140. The projection system 160 can additionally or alternatively store these image projection settings in local memory on the helmet system 100.

In the variation of the helmet system 100 that includes a forward-facing camera, the projection system 160 can implement similar methods and techniques to generate images from video frames output by the forward-facing camera 151, to manipulate these images, and to display these images on the secondary visor 140. For example, the helmet system 100 can include a forward-facing thermal imaging sensor, and the projection system 160 can implement the foregoing methods and techniques to render thermal images on the secondary visor 140, such as at night, when an ambient light level proximal the shell 110 drops below an ambient light level, or in response to an input selection for an augmented thermal video stream on the secondary visor 140 entered by the user.

1.11 Light Control

In one variation, the secondary visor 140 includes an active tinting panel, and the helmet system 100 further includes: an ambient light sensor 121 arranged within the interior volume in of the shell 110; and a controller electrically coupled to the active tinting panel and configured to adjust an opacity of the secondary visor 140 based on an output of the ambient light sensor 121. Generally, in this variation, the secondary visor 140, the ambient light sensor 121, and the controller cooperate to actively adjust the opacity of the secondary panel to ensure that content displayed on the secondary visor 140 remains visually accessible by the user across a range of ambient lighting conditions.

In this variation, the ambient light sensor 121 can include a photo detector arranged inside the interior volume in of the shell 110, such as adjacent the user's temple and projected toward the aperture 112, and the controller can sample the photo detector to determine a real-time light level within the helmet system 100 proximal the user's eyes. In this variation, the active tinting panel can include a liquid crystal layer disposed across (or within) the transparent member of the secondary visor 140. For example: a first polarizing film can be applied across a first side of the transparent member; a common electrode plane of indium-tin oxide can be applied to the second (i.e., opposite) side of the transparent member; a layer of liquid crystal substance can be applied over the common electrode plane and enclosed with a transparent cover (e.g., a glass polycarbonate cover); and a second polarizing film can be applied over the transparent cover—at a right angle to the first polarizing film—to form a tintable liquid crystal layer over the transparent member of the secondary visor 140. The controller can then automatically adjust the opacity of the secondary visor 140 by passing a current through the common electrode plane. In particular, in this example, the controller can pass a current of magnitude proportion to the detected ambient light level in the interior volume in of the shell 110 to match an opacity of the secondary visor 140 to the current ambient light level. The controller can read the photo detector (or other ambient light sensor 121) and modify the opacity of the secondary visor 140 in real-time during use. Furthermore, in this variation, the primary visor 130 can include a polarized translucent polymer screen, and the photo detector can be oriented perpendicular to the polarity of the polarized translucent polymer screen or arranged in the helmet system 100 in any other suitable way. Alternatively, the controller can set the opacity of the secondary visor 140 based on a manual input received at the helmet system 100 or received at an external device (e.g., a smartphone) wirelessly connected to the helmet system 100.

Yet alternatively, in the foregoing variation, the primary visor 130 can include an active tinting panel, such as a tintable liquid crystal layer arranged over a transparent polycarbonate substrate, and the controller can selectively adjust the opacity of the active tinting panel based on ambient light levels detected in the interior volume in of the shell 110, as described above.

The projection system 160 can additionally or alternatively modify a light output level from the projector 161 dynamically—based on the ambient light levels detected in the interior volume in of the shell 110—to preserve visibility of images projected onto (or through) the secondary visor 140 across a range of exterior lighting conditions.

The primary visor 130 and/or the secondary visor 140 can additionally or alternatively include a photochromic polymer layer that exhibits reduced transparency when exposed to higher levels of ambient light (e.g., ultraviolet light). For example, the primary visor 130 can exclude a photochromic polymer layer, and the secondary visor 140 can include a photochromic polymer layer such that ambient light can pass through the primary visor 130 to the secondary visor 140, which can darken the secondary visor 140 under certain (e.g., high-intensity) lighting conditions. Furthermore, in this example, the photochromic polymer layer of the secondary visor 140 can be sensitive to light output from the projection system 160 such that the secondary visor 140 darkens when an image is projected thereonto, thereby improving local contrast between the secondary visor 140 and the image and improving visibility of the image.

However, the helmet system 100 can include any other active or passive ambient light control elements or subsystems.

2. Methods

Figure 9:
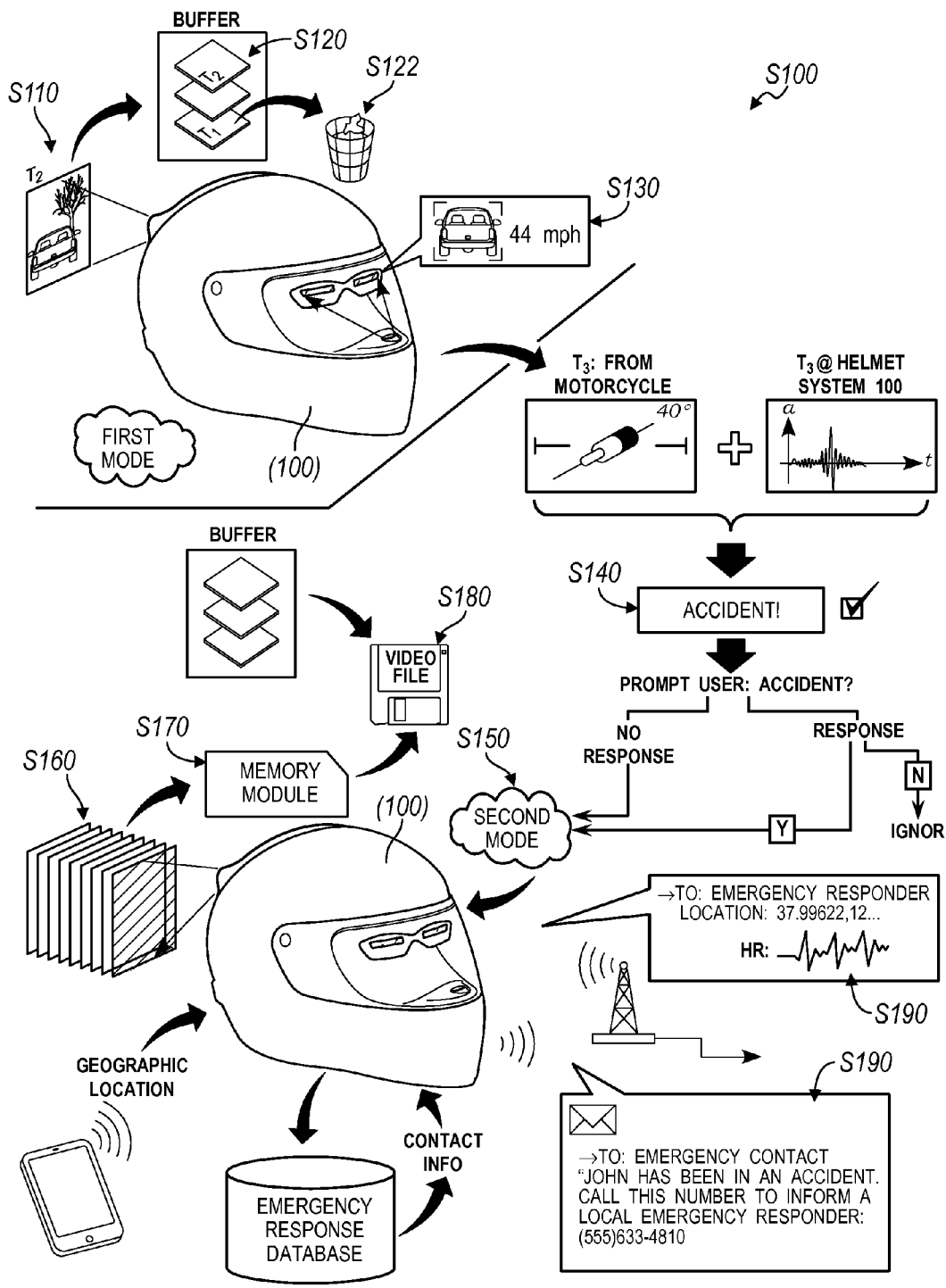
FIG. 9 is a flowchart representation of a method.

As shown in FIG. 9, a method S100 for recording accidents includes, in a first mode: with a camera arranged on a helmet, capturing a second video frame at a second time in Block S110; storing the second video frame with a first sequence of video frames in local memory in the helmet in Block S120, the first sequence of video frames captured over a period of time corresponding to a buffer duration; in response to capturing the second video frame, removing a first video frame from local memory in Block S122, the first video frame captured at a first time preceding the second time by a duration exceeding the buffer duration; and at approximately the second time, rendering a subregion of the second video frame on a display arranged within the helmet in Block S130. The method S100 further includes: based on an output of an inertial sensor arranged within the helmet, detecting an accident involving the helmet in Block S140; in response to detecting the accident, transitioning from the first mode into a second mode in Block S150; in the second mode, with the camera, capturing a second sequence of video frames in Block S160, and storing the second sequence of video frames in local memory in the helmet in Block S170, the second sequence of video frames corresponding to a period of time exceeding the buffer duration; and generating a video file from the first sequence of video frames and the second sequence of video frames stored in local memory in Block S180.

2.1 Applications

Generally, the method S100 can be executed by the helmet system 100 described above: to capture video frames of field to the posterior of the helmet system 100 (e.g., behind the user) with a rear-facing camera 150; to display forms (e.g., rectified, cropped, and mirrored forms) of these video frames substantially in real-time on a display within the helmet system 100; to fill and update a limited duration of most-recent original or modified video frames in a buffer in local memory; and, in response to an accident or impact involving the helmet system 100, to record video frames captured by the rear-facing camera 150 indefinitely until stopped manually or until local memory is full. In particular, the helmet system 100 can execute Blocks of the method S100 to capture video of the rear field behind the helmet system 100—with a rear-facing camera 150—for real-time consumption by the user, such as while riding a motorcycle or snowboarding and to store in memory video frames dating back a limited duration from current (e.g., fifteen seconds) in the first mode. According to the method S100, the helmet system 100 can then enter the second mode in response to detection of an accident or impact involving the helmet system 100, then record and store video of extended duration (e.g., unlimited, bounded only by memory size and human immobilization) with the same rear-facing camera 150 in the second mode, and package pre-accident and post-accident video for asynchronous consumption. The helmet system 100—executing the method S100—can therefore leverage the rear-facing camera 150 to capture video frames for real-time consumption by the user before an accident and to capture video frames for asynchronous consumption after the accident.

In the second mode, the helmet system 100 can also: interface with the user to confirm or discard accident detection; push accident data and alerts to a local emergency responder or to an emergency contact (previously) elected by the user; host a call to an emergency responder or to an emergency contact; stream biometric data recorded locally at the helmet system 100 or received from a connected wearable device to an external entity (e.g., a local emergency responder, an emergency contact); and store biometrics data with video data in local memory. The helmet system 100 can therefore execute Blocks of the method S100 independently and/or in cooperation with an external device (e.g., a wireless-enabled vehicle, a smartphone, a wearable device) to collect and distribute post-accident data to select entities.

2.2 First Mode

Block S110 of the method S100 recites, in a first mode, capturing a second video frame at a second time with a camera arranged on a helmet. Generally, the helmet system 100 can execute Block S110 to capture a newest video frame—in a sequence of video frames—through one or more cameras arranged on the helmet system 100. For example, as described above, the helmet system 100 can include a single camera arranged on the shell 110 of the helmet system 100, defining a field of view extending outwardly from the posterior end of the shell 110, and including a wide-angle lens. Alternatively, the helmet system 100 can include multiple cameras, and the helmet system 100 can stitch multiple frames captured by the set of cameras in a single sampling period into a single flat or three-dimensional rectified video frame. However, the helmet system 100 can capture a rear-field video frame with any other optical sensor and in any other way in Block S110.

Block S120 of the method S100 recites storing the second video frame with a first sequence of video frames in local memory in the helmet, wherein the first sequence of video frames was captured over a period of time corresponding to a buffer duration. Furthermore, Block S122 of the method S100 recites, in response to capturing the second video frame, removing a first video frame from local memory, wherein the first video frame was captured at a first time preceding the second time by a duration exceeding the buffer duration. Generally, the helmet system 100 functions to add a video frame newly captured by the rear-facing camera 150 to the buffer in local memory in Block S120 and to remove an oldest video frame from the buffer in Block S122. For example, the helmet system 100 can store a sequence of newest video frames spanning a static buffer duration of fifteen seconds. The helmet system 100 can implement an adjustable or dynamic buffer duration, such as a buffer duration set manually by the user (e.g., through a wirelessly-connected smartphone) or a buffer duration (inversely) proportional to road speed.

The helmet system 100 can write a newest video frame—as captured by the camera 150—to the buffer in local memory in the helmet system 100 (e.g., arranged inside the fairing 120) substantially in real-time once the video frame is captured. The helmet system 100 can additionally or alternatively upload the newest video frame to a buffer in memory in an external device. For example, the helmet system 100 can store the newest video frame to a primary buffer in local memory in the helmet system 100 and wirelessly transmit a copy of the newest video frame to a smartphone—wirelessly paired to the helmet system 100—for storage in a backup buffer in memory in the smartphone. The helmet system 100 can additionally or alternatively write a processed form of the newest video frame to the local (and/or remote) buffer. For example, the helmet system 100 can dewarp, compress, crop, or color-adjust the original video frame to generate a rectified video frame or an image for display on the secondary visor 140, as described above, and the helmet system 100 can write the rectified video frame or the image to the buffer. However, the helmet can store the newest video frame in any other format and in any in the buffer.

Block S130 of the method S100 recites, at approximately the second time, rendering a subregion of the second video frame on a display arranged within the helmet. Generally, in Block S130, the helmet system 100 executes methods and techniques described above to dewarp, compress, crop, or modify the newest video frame in any other way to generate an image for immediate display on the secondary visor 140 (or other display) within the helmet system 100 in the first mode.

2.3 Accident Detection

Block S140 of the method S100 recites, based on an output of an inertial sensor arranged within the helmet, detecting an accident involving the helmet; and Bock S150 of the method S100 recites, in response to detecting the accident, transitioning from the first mode into a second mode. Generally, the helmet system 100 functions to detect an impact or accident involving the helmet in Block S140 and to enter the second mode (e.g., an "accident response" mode) in Block S150.

In one implementation, a processor 124 within the helmet system 100 samples outputs of an accelerometer and/or a gyroscope arranged within the helmet system 100 (e.g., within the fairing 120) and determines occurrence of an impact (or an accident) in response to a measured acceleration (less gravity) exceeding a threshold acceleration. For example, for the helmet system 100 defining a motorcycle helmet, the processor 124 can store a threshold acceleration of 14 m/s$^2$, which may exceed a maximum acceleration that a motorcycle may encounter—even under heavy throttle and heavy braking—during use, and the processor 124 can determine that the helmet system 100 has been involved in an accident if an output of an onboard accelerometer indicates that the helmet system 100 has been exposed to an absolute acceleration exceeding 14 m/s$^2$.

The processor 124 can additionally or alternatively detect an impact or accident based on data received from an external device. For example, the helmet system 100 can: wirelessly pair with a motorcycle; download tilt (i.e., roll) angle data from the motorcycle during operation; and correlate a tilt angle outside of an operating roll angle range with an accident, as shown in FIG. 9. The processor 124 can also merge data received from an external device with data collected locally. In the foregoing example, the processor 124 can dynamically adjust the operating roll angle range based on (e.g., proportionally with) acceleration data collected locally, including discarding a high tilt angle of 50° during a period of acceleration above 8 m/s$^2$ as not an accident but determining an accident for a lower tilt angle of 40° during a period of acceleration below 1 m/s$^2$. The processor 124 can also match changes in telemetry data received from the motorcycle with changes in inertial data collected locally in time, and the helmet system 100 can fuse these data from local and external sensors to confirm the accident. For example, the processor 124 can confirm an accident at the helmet system 100 based on a change in the telemetry data received from the motorcycle and occurring at a particular time within a threshold duration of a change in outputs of an internal inertial sensor (e.g., an accelerometer integrated into the helmet system 100). The processor 124 can implement similar methods and techniques to collect and processor 124 inertial, geospatial position, and/or other data recorded by a mobile computing device (e.g., a smartphone) wirelessly-connected to the helmet system 100.

Alternatively, in Block S140, the helmet system 100 can receive an accident trigger directly from an external device (e.g., a smartphone, a motorcycle) wirelessly-connected to the helmet system 100. For example, a motorcycle or smartphone can execute the foregoing methods and techniques to detect an accident and can then wirelessly-broadcast an accident trigger to the helmet system 100 in Block S140.

Once an accident is detected locally or once an accident trigger is received from an external device, the helmet system 100 can further prompt the user to confirm or discard the detected accident, as shown in FIG. 9. For example, in response to a detected accident or accident trigger, the helmet system 100 can activate a haptic actuator (e.g., a vibrator) within the helmet, issue an audible prompt through one or more speakers integrated into the helmet system 100, and/or render a visual prompt on the secondary visor 140 (or other display within the helmet system 100) to indicate to the user that a possible accident was detected.

In one implementation, the helmet system 100: sets a timer for a limited duration (e.g., ten seconds) in response to detection of an accident; issues a haptic prompt, an audible prompt, and/or a visual prompt to cue the user to discard the accident detection before expiration of the timer—such as via a manual input region 122 on the helmet system 100 or through a native helmet controls application executing on a connected mobile computing device or via voice controls supported by the helmet system 100 and/or the connected mobile computing device; discards the detected accident if a discard input is entered by the user; immediately transitions into the second mode in Block S150 if accident confirmation is entered by the user; and transitions into the second mode in Block S150 in response to expiration of the timer if no discard or confirmation input is received from the user. The helmet system 100 can therefore deliver a prompt to the user through an output module within the helmet system 100 in response to a detected accident and then confirm the accident in response to absence of manual acknowledgement of the prompt within a threshold period of time from delivery of the prompt. Alternatively, the helmet system 100 can automatically enter the second mode in Block S150 and execute various Blocks of the method S100 in the second mode accordingly in response to an accident trigger, and the helmet system 100 can transition back into the first mode, into a standby mode, etc. in response to subsequent input by the user to cancel or discard the accident trigger.

However, the helmet system 100 can implement any other suitable method or technique to detect and/or confirm an accident or impact involving the helmet system 100.

2.4 Second Mode

Block S160 of the method S100 recites, with the camera, capturing a second sequence of video frames in the second mode in Block S160; and Block S170 of the method S100 recites storing the second sequence of video frames in local memory in the helmet in the second mode in Block S170, wherein the second sequence of video frames corresponds to a period of time exceeding the buffer duration. Generally, in Blocks S160 and S170, the helmet system 100 functions to capture a rolling video feed through the rear-facing camera 150 and to write this video feed of extended duration to local and/or remote memory. In particular, once the helmet system 100 enters the second mode, the helmet system 100 can record a video feed—from the rear-facing camera 150—duration limited by local memory size and/or a user input to cease recording rather than by a buffer of limited duration. For example, the helmet system 100 can store a first video feed limited to fifteen seconds in duration in the first mode, and the helmet system 100 can store a second video feed of several minutes or hours once an accident is detected and ceasing only at the earlier of consumption of all local memory in the helmet system 100 and a user input to cease recording.

As in Block S120, the helmet system 100 can additionally or alternatively upload video frames to an external device (e.g., a smartphone, a remote server or database) in Block S170. However, the helmet system 100 can record and store a second sequence of video frames captured over a period of unmetered duration in any other suitable way in Blocks S160 and S170.

2.5 Additional Data

In one variation, the helmet system 100: captures additional data through local sensors integrated into the helmet system 100 and/or through sensors integrated into a wirelessly-connected external device; writes these data to the buffer in the first mode; and records a feed of these data in local memory in the second mode.

In one implementation, the helmet system 100 includes one or more biometric sensors—such as a heart rate sensor, a skin temperature sensor, a pulse oximetry sensor, and/or a set of dry electroencephaly sensors. In this implementation, the helmet system 100 samples outputs of a biometric sensor during operation, writes a newest biometric value from the biometric sensor to the buffer, and discards an oldest biometric value from the buffer in order to maintain and update a feed of newest biometric data in the buffer. For example, in the first mode, the helmet system 100 can: recording a second biometric value at the second time; store the second biometric value with a first sequence of biometric values—recorded over a period of time corresponding to the first sequence of video frames—in local memory; and, in response to recording the second biometric value, removing a first biometric value recorded at the first time from local memory. The helmet system 100 can therefore match a biometric feed to a video feed in time and store these discrete data feeds in the buffer in the first mode (e.g., in Blocks S120 and S122).

In the foregoing implementation, the helmet system 100 can write values from one or more biometric sensors integrated into the helmet system 100 to the buffer in local memory. The helmet system 100 can additionally or alternatively download biometric data from an external device connected to the helmet system 100. For example, the helmet system 100 can stream heart rate data from a wearable device worn by the user and wirelessly connected to the helmet system 100. The helmet system 100 can additionally or alternatively upload biometric data to an external device for storage in an external buffer, such as in memory in a connected smartphone or in a remote database.

The helmet system 100 can implement similar methods and techniques to record telemetry data to the buffer, such as road speed, direction, location, altitude, pitch angle, yaw angle, roll angle, lateral and longitudinal accelerations, etc. For example, the helmet system 100 can: wirelessly pair with a motorcycle; download telemetry data from the motorcycle, including engine speed, ground speed, and/or tilt (i.e., roll) angle during use; and write these telemetry data to the buffer. Similarly, the helmet system 100 can download geographic location data from a smartphone wirelessly-connected to the helmet system 100 and can write these geographic location data to the buffer. Furthermore, the helmet system 100 can sample internal inertial sensors 125, environmental sensors, etc. and write these data to the buffer in Blocks S120 and S122.

In one implementation in which the helmet system 100 further includes a forward-facing camera 151, the helmet system 100 can also record video frames captured by the forward-facing camera 151 to the buffer in Blocks S110, S120, and S122. For example, the forward-facing camera 151 can be operable between a buffer mode and an action mode. In this example, in the first mode, the helmet system 100 can write a newest video frame from the forward-facing camera 151 to the buffer and discard an oldest forward-facing video frame from the buffer to maintain and update a feed of forward-facing video frames of limited duration (e.g., fifteen seconds) when the forward-facing camera 151 is in the buffer mode. However, when the forward-facing camera 151 is in the action mode, the helmet system 100 can write a continuous video feed—of duration unrelated to the buffer—to local memory in the first mode.

In the foregoing implementations, when the helmet system 100 enters the second mode, the helmet system 100 can record continuous streams of biometric data, telemetry data, environmental data, and/or forward-facing video frames, etc. to local memory, such as until local memory is full or until the helmet system 100 is shut down.

2.6 Accident Video

Block S180 of the method S100 generating a video file from the first sequence of video frames and the second sequence of video frames stored in local memory. Generally, in Block S180, the helmet system 100 functions to package video and/or other data written to the buffer in the first mode with data feeds recorded during the second mode.

In one implementation, the helmet system 100 combines the first sequence of video frames from the first mode and the second sequence of video frames from the second mode to generate a single local video file. The helmet system 100 can write this local video file to a removable memory drive and/or upload the local video file to a remote device, such as to a desktop computer over a wired connection or to a remote server over a cellular or other wireless radio connection.

In another implementation, the helmet system 100 combines a first sequence of video frames and a first sequence of biometric values stored in the buffer and a second sequence of video frames and a second sequence of biometric values recorded during the second mode into a multimedia file spanning the accident, including the buffer duration (e.g., fifteen seconds) before the accident and a recording period following the accident. The helmet system 100 can also incorporate sequences of telemetry data, environmental data, and/or forward-facing video frames, etc. into the multimedia file in Block S180. For example, in Block S180, the helmet system 100 can: combine a forward-facing video frame and a rear-facing video frame recorded at substantially identical times into a single composite video frame as applicable for forward-facing and rear-facing video frames stored in the buffer in the first mode; assemble the composite video frames from the buffer into a first composite video stream; apply similar methods and techniques as application to forward-facing and rear-facing video frames written to memory in the second mode to assemble a second composite video stream; and then align the first composite video stream and the second composite video stream in time to generate a single multimedia file. In this example, the helmet system 100 can also generate visual graphs representing acceleration, speed, heart rate, etc. relative to time for each sensor sampling period recorded to the buffer and to local memory in the first and second modes, and the helmet system 100 can combine these visual graphs with video frames captured at corresponding times to generate composite video frames.

However, the helmet system 100 can implement any other method or technique to assemble a video or multimedia file containing pre- and post-accident data. The helmet system 100 can then asynchronously upload the single multimedia file to an external computer system.

2.7 Emergency Response

One variation of the method S100 includes automatically contacting an external entity in response to detection of an accident involving the helmet in Block S190, as shown in FIG. 9. Generally, in Block S190, the helmet system 100 functions to automatically transmit accident data to one or more external contacts in response to detection of the accident in Block S140.

In one implementation, in response to detecting the accident in Block S140, the helmet system 100: retrieves a geographic location, such as from a smartphone wirelessly-connected to the helmet system 100; retrieves contact information for a local emergency responder from an emergency response database—such as accessed from a remote database via the smartphone—based on the geographic location of the helmet system 100; generates a textual accident alert including the contact information for the local emergency responder, the geographic location, and/or rider identification information stored in memory in the helmet system 100 or in the smartphone; and transmits the textual accident alert to a remote computer system for delivery to a preset contact, such as to a parent or spouse directly through a cellular tower or through the smartphone, as shown in FIG. 9. In this implementation, the helmet system 100 can address the textual accident alert to a family contact, a friend, a guardian, or to any other one or more contacts stored in local memory in the helmet system 100. The helmet system 100 can broadcast the textual accident alert with delivery address (e.g., phone number, email address) directly to a remote server, such as over a cellular network, or pass the textual accident alert to the smartphone or other connected device for subsequent distribution to a remote server. Alternatively, the helmet system 100 can pass relevant data to a local external device—such as a smartphone executing native helmet controls application as described above—that implements similar methods and techniques to generate and distribute a textual accident alert to one or more preselected contacts.

In another implementation, the helmet system 100 automatically calls an emergency responder in response to detection of the accident in Block S140. For example, the helmet system 100 can pair with a smartphone carried by the user, automatically initiate a call to a local emergency responder through the smartphone, output audio signals received from the call through integrated speakers, and output audio signals recorded by an integrated microphone to the smartphone during the call. In particular, in this example, the helmet system 100 can: broadcast, to a mobile computing device wirelessly connected to the helmet, a trigger to initiate a phone call to a local emergency responder contact in response to detecting the accident; output audio signals received from the mobile computing device during the phone call; and transmit audio signals recorded at the helmet to the mobile computing device during the phone call. Similarly, the helmet system 100 can pass relevant data to the smartphone executing a native helmet controls application to enable the smartphone to generate call resources and to place a call to a local emergency responder or other contact in response to detection of an accident involving the helmet system 100. The helmet system 100 can thus automatically initiate a phone call to an emergency responder on behalf of the user and then enable the user to communicate with a human dispatcher immediately through the helmet system 100 (and without requiring the user to remove the helmet system 100 and retrieve his smartphone). Alternatively, the helmet system 100 can submit an automated emergency response request to the emergency responder. For example, the helmet system 100 or the mobile computing device executing the native helmet controls application can access a prerecorded emergency request audio resource, insert real data into the audio resource, such as the user's name, location, and recorded magnitude of impact, and replay this customized audio file during a phone call placed to an emergency responder. Similarly, the helmet system 100 can access a prerecorded emergency request textual communication, insert real data into the textual communication, and transmit this customized textual communication to emergency responder, such as in the form of an email or text message.

In the foregoing implementation, the helmet system 100 selectively executes these user-involved and fully-automated emergency response request methods. For example, the helmet system 100 can default to fully-automated emergency response request methods but selectively, alternately implement user-involved emergency response request if the user provides a manual input indicating ability to manage the accident once the accident is detected.

In this variation, the helmet system 100 can also stream data collected locally at the helmet system 100 and/or by a connected external device (e.g., a wearable device) to a remote computer system, as shown in FIG. 9. For example, in response to detection of an accident in Block S140, the helmet system 100 can stream heart rate data, acceleration data (indicating the user' motion), electroencephalogy data, and live video feeds from the rear-facing and/or the front-facing camera in the helmet system 100 to an emergency responder once an (audible or textual) emergency response request has been sent to the emergency responder. The helmet system 100 can transmit these data directly to the emergency responder, such as via the Internet by uploading these data to an Internet-connected cellular tower over wireless communication protocol. Alternatively, the helmet system 100 can upload these data to a connected mobile computing device (e.g., smartphone) substantially in real-time, and the smartphone can selectively distribute these data to the emergency responder or other entity. Furthermore, the helmet system 100 (and/or the mobile computing device) can prioritize transmission of the select data to the emergency responder or other contact, such as based on wireless communication bandwidth. For example, the helmet system 100 can prioritize transmission of geographic location data over biometric sensor data, prioritize biometric sensor data over accelerometer data, prioritize accelerometer data, and prioritize accelerometer data over video frames recorded at the helmet system 100 when transmitting data to the emergency responder.

However, the helmet system 100 can function in any other way—independently or in cooperation with an external device—to transmit accident-related data to an external entity in response to detection of an accident in Block S140.

The systems and methods of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method comprising:
in a first mode:
with a camera arranged on a helmet, capturing a second video frame at a second time;
storing the second video frame with a first sequence of video frames in local memory in the helmet, the first sequence of video frames captured over a period of time corresponding to a buffer duration;
in response to capturing the second video frame, removing a first video frame from local memory, the first video frame captured at a first time preceding the second time by a duration exceeding the buffer duration; and
at approximately the second time, rendering a subregion of the second video frame on a display arranged within the helmet;
based on an output of an inertial sensor arranged within the helmet, detecting an accident involving the helmet;
in response to detecting the accident, transitioning from the first mode into a second mode;
in the second mode:
with the camera, capturing a second sequence of video frames; and
storing the second sequence of video frames in local memory in the helmet, the second sequence of video frames corresponding to a period of time exceeding the buffer duration; and
generating a video file from the first sequence of video frames and the second sequence of video frames stored in local memory.

2. The method of claim 1, wherein storing the second video frame in local memory comprises storing the first sequence of video frames captured over the buffer duration of approximately fifteen seconds; and wherein storing the second sequence of video frames in local memory comprises storing the second sequence of video frames in local memory captured over a period of unmetered duration.

3. The method of claim 1, wherein detecting the accident comprises:
delivering a prompt through an output module within the helmet in response to the output of the inertial sensor exceeding a threshold output value; and
detecting an accident involving the helmet in response to absence of manual acknowledgement of the prompt within a threshold period of time from delivery of the prompt.

4. The method of claim 1, wherein detecting the accident comprises downloading telemetry data from an external computer system wirelessly connected to the helmet and confirming the accident based on change in the telemetry data occurring at a particular time within a threshold duration of a change in outputs of the inertial sensor.

5. The method of claim 4, wherein downloading telemetry data from the external computer system comprises downloading lean angle sensor data from a vehicle wirelessly connected to the helmet and downloading accelerometer data from a mobile computing device wirelessly connected to the helmet.

6. The method of claim 1,
wherein capturing the second video frame in the first mode and capturing the second sequence of video frames in the second mode comprise capturing the second video frame and capturing the second sequence of video frames through the camera facing outwardly from a posterior end of the helmet;
further comprising, in the first mode, recording a first continuous video stream through a second camera arranged on the helmet and facing outwardly from an anterior end of the helmet;
further comprising, in the second mode, recording a second continuous video stream through the second camera; and
wherein generating the video file comprises generating a first composite video stream of composite video frames from the first sequence of video frames and the first continuous video stream, generating a second composite video stream of composite video frames from the second sequence of video frames and the second continuous video stream, and aligning the first composite video stream and the second composite video stream in time to generate the video file.

7. The method of claim 1, wherein rendering the subregion of the second video frame on the display in the first mode comprises:
dewarping the second video frame to generate a rectified digital photograph;
applying a crop area to the rectified digital photograph to generate an image;
mirroring the image; and
projecting the image onto a secondary visor arranged within helmet substantially at the second time.

8. The helmet system of claim 7, further comprising, in the first mode:
calculating a pitch angle of the helmet based on outputs of the inertial sensor;
modulating the vertical position of the crop area across rectified digital photographs corresponding to a series of video frames captured by the camera based on pitch angles of the helmet determined at corresponding times; and
locking the vertical position of the crop area within rectified digital photographs corresponding to a subsequent series of video frames captured by the camera in response to selection of an input region on the helmet.

9. The method of claim 1, further comprising, in response to detecting the accident:
retrieving a geographic location of the helmet;
retrieving a local emergency response contact from an emergency response database based on the geographic location;
generating a textual accident alert comprising the local emergency response contact, the geographic location, and rider identification information stored in local memory; and
transmitting the textual accident alert to a remote computer system for delivery to a family contact stored in local memory.

10. The method of claim 1, further comprising:
in response to detecting the accident, broadcasting, to a mobile computing device wirelessly connected to the helmet, a trigger to initiate a phone call to a local emergency response contact;

in the second mode, at the helmet, outputting audio signals received from the mobile computing device during the phone call; and in the second mode, transmitting audio signals detected at the helmet to the mobile computing device during the phone call.

11. The method of claim 1, further comprising, in the second mode, streaming an output of a biometric sensor installed in the helmet to an external computer system.

12. The method of claim 11, wherein streaming the output of the biometric sensor in the second mode comprises streaming an output of a electroencephalogy sensor integrated into the helmet to a mobile computing device over wireless communication protocol.

13. The method of claim 11, further comprising, in the second mode, wirelessly streaming select video frames from the second sequence of video frames to the external computer system; wherein streaming the output of the biometric sensor and streaming select video frames to the external computer system comprise prioritizing transmission of the output of the biometric sensor over video frames to the external computer system according to available wireless communication bandwidth.

14. The method of claim 1, further comprising:
in the first mode:
through a biometric sensor in communication with the helmet, recording a second biometric value at the second time;
storing the second biometric value with a first sequence of biometric values in local memory, the first sequence of biometric values recorded over a period of time corresponding to the first sequence of video frames; and
in response to recording the second biometric value, removing a first biometric value recorded at the first time from local memory; and
in the second mode, storing outputs of the biometric sensor over a period of time corresponding to the second sequence of video frames in local memory;
wherein generating the video file comprises combining the first sequence of video frames, the second sequence of video frames, the first sequence of biometric values, and the second sequence of biometric values stored in local memory into a multimedia file spanning the accident.

15. The method of claim 1, further comprising:
in the first mode:
through the inertial sensor in the helmet, recording a second telemetric value at the second time;
storing the second telemetric value with a first sequence of telemetric values in local memory, the first sequence of telemetric values recorded over a period of time corresponding to the first sequence of video frames; and
in response to recording the second telemetric value, removing a first telemetric value recorded at the first time from local memory; and
in the second mode, storing outputs of the telemetric sensor over a period of time corresponding to the second sequence of video frames in local memory;
wherein generating the video file comprises combining the first sequence of video frames, the second sequence of video frames, the first sequence of telemetric values, and the second sequence of telemetric values stored in local memory into a multimedia file spanning the accident.

16. The method of claim 1, wherein generating the video file comprises aligning the first sequence of video frames and the second sequence of video frames in time; and further comprising asynchronously uploading the single video file to an external computer system.

17. A method comprising:
in a first mode:
with an optical sensor coupled to and defining a field of view extending outwardly from a posterior end of the helmet, capturing a second video frame at a second time;
storing the second video frame with a first sequence of video frames in local memory in the helmet, the first sequence of video frames captured over a period of time corresponding to a buffer duration;
in response to capturing the second video frame, removing a first video frame from local memory, the first video frame captured at a first time preceding the second time by a duration exceeding the buffer duration; and
at approximately the second time, rendering a subregion of the second video frame on a display arranged within the helmet;
in response to detection of an accident involving the helmet, transitioning from the first mode into a second mode;
in the second mode:
with the camera, capturing a second sequence of video frames; and
storing the second sequence of video frames in local memory in the helmet, the second sequence of video frames corresponding to a period of time exceeding the buffer duration; and
assembling a video file comprising the first sequence of video frames and the second sequence of video frames stored in local memory; and
uploading the video file to an external computer system.

18. The method of claim 17, further comprising receiving a trigger from a mobile computing device wirelessly connected to the helmet, the trigger indicating instance of the accident.

19. The method of claim 17,
further comprising, in the second mode, recording a continuous video stream through a second camera coupled to and defining a field of view extending outwardly from an anterior end of the helmet;
wherein assembling the video file comprises generating a composite video stream of composite video frames from the second sequence of video frames and the continuous video stream and aligning the first sequence of video frames and the second composite video stream in time to generate the video file.

20. The method of claim 17, wherein storing the second video frame in local memory comprises storing the first sequence of video frames captured over the buffer duration of approximately fifteen seconds; and wherein storing the second sequence of video frames in local memory comprises storing the second sequence of video frames in local memory captured over a period of unmetered duration.

21. The method of claim 17,
wherein storing the second video frame with the first sequence of video frames comprises storing the second video frame comprising a wide-angle video frame in local memory; and
wherein rendering the subregion of the second video frame on the display in the first mode comprises:

dewarping the wide-angle video frame to generate a rectified digital photograph;
applying a crop area to the rectified digital photograph to generate an image;
mirroring the image; and
projecting the image onto a secondary visor arranged within helmet substantially at the second time.

\* \* \* \* \*